United States Patent [19]

Kosley, Jr. et al.

[11] Patent Number: 5,145,855

[45] Date of Patent: Sep. 8, 1992

[54] 6- AND 7-DEOXYFORSKOLIN AND DERIVATIVES THEREOF

[75] Inventors: Raymond W. Kosley, Jr., Bridgewater; Bettina Spahl, Edison, both of N.J.

[73] Assignee: Hoechst Roussel Pharmaceuticals, Inc., Somerville, N.J.

[21] Appl. No.: 792,884

[22] Filed: Nov. 15, 1991

Related U.S. Application Data

[62] Division of Ser. No. 376,383, Jul. 6, 1989, Pat. No. 5,093,336.

[51] Int. Cl.$^5$ .................. A61K 31/505; A61K 31/52; A61K 31/54; A61K 31/50; C07D 311/92

[52] U.S. Cl. .................... 514/269; 514/183; 514/211; 514/212; 514/218; 514/228.2; 514/228.5; 514/232.5; 514/232.8; 514/253; 514/316; 514/320; 514/321; 514/333; 514/338; 514/369; 514/376; 514/397; 514/385; 514/422; 514/432; 514/452; 514/453; 514/455; 549/13; 549/228; 549/214; 549/358; 549/389

[58] Field of Search .......... 514/269, 183, 218, 232.5, 514/316, 333, 376, 422, 453; 540/480, 544, 601; 544/265, 318, 69, 121, 130, 137, 150, 229, 238, 369

[56] References Cited

U.S. PATENT DOCUMENTS

| | | | |
|---|---|---|---|
| 4,088,659 | 5/1978 | Bhat et al. | 260/345.2 |
| 4,118,508 | 10/1978 | Bhat et al. | 424/283 |
| 4,134,986 | 1/1979 | Bajwa et al. | 424/283 |
| 4,476,140 | 10/1984 | Sears et al. | 424/283 |
| 4,517,200 | 5/1985 | Kruetner et al. | 514/455 |
| 4,564,626 | 1/1986 | Kruetner et al. | 514/430 |
| 4,639,443 | 1/1987 | Kosley, Jr. et al. | 514/222 |
| 4,639,446 | 1/1987 | Kosley, Jr. et al. | 514/222 |
| 4,666,904 | 5/1987 | Kosley, Jr. et al. | 514/222 |
| 4,672,115 | 6/1987 | Kosley, Jr. et al. | 544/58.2 |
| 4,673,752 | 6/1987 | Kosley, Jr. et al. | 549/389 |
| 4,677,103 | 6/1987 | Kosley, Jr. et al. | 514/222 |

FOREIGN PATENT DOCUMENTS

| | | |
|---|---|---|
| 0126313A2 | 11/1984 | European Pat. Off. . |
| 0189801A1 | 8/1986 | European Pat. Off. . |
| 0192056A1 | 8/1986 | European Pat. Off. . |
| 3346869A1 | 7/1984 | Fed. Rep. of Germany . |
| 3407514A1 | 9/1985 | Fed. Rep. of Germany . |
| 3502686A1 | 8/1986 | Fed. Rep. of Germany . |

OTHER PUBLICATIONS

J. Caprioli et al., "Foreskolin Lowers Intraocular Pressure by Reducing Aqueous Inflow", Invest. Ophtalmol. & Vis. Sci., 25, 268–277 (1984).

N. de Souza et al., "Forskolin: A Labdane Diterpenoid with Antihypertensive, Positive Inotropic, Platelet Aggregation Inhibitory, and Adenylate Cyclase Activating Properties", Med. Res. Rev., 3(2), 201–219 (1983).

S. Bhat et al., "The Antihypertensive and Positive Inotropic Diterpene Forskolin: Effects of Structural Modifications on its Activity", J. Med. Chem., 26, 486–492 (1983).

K. Seamon et al., "Structure–Activity Relationships for Activation of Adenylate Cyclase by the Diterpene Forskolin and its Derivatives", J. Med. Chem., 26(3), 436–439 (1983).

S. Bhat et al., "Reaction of Forskolin, a Biologically Active Diterpenoid from Coleus forskohlii", J. Chem. Soc., Perkin I, 767–771 (1982).

K. Seamon and J. Daly, "Activation of Adenylate Cyclase by the Diterpene Forskolin Does Not Require the Guanine Nucleotide Regulatory Protein", J. Bio. Chem., 256(19), 9799–9801 (1981).

J. Takeda et al., "Forskolin Activates Adenylate Cyclase Activity and Inhibits Mitosis in In Vitro in Pig Epidermis", J. Investig. Derm., 81(3), 236–240 (1981).

K. Seamon et al., "Forskolin: Unique Diterpene Activator of Adenylate Cyclase in Membranes and in Intact Cells", Proc. Natl. Acad. Sci., 78(6), 3363–3367 (1981).

S. Bhat et al., "Structures and Stereochemistry of New Labane Diterpenoids from Coleus forskohlii Brig.", Tet. Lett., No. 19, 1669–1672 (1977).

Derwent Citation 85-223308/36, 231 "Treatment of Hyperplastic Skin Diseases, Especially Psoriasis, by Topical Application of Labdane Derivatives, Especially Forskolin".

Barton et al., JCS, Perkin I, pp. 1574–1585 (1975).
Barton et al., JCS, Perkin I, pp. 1718–1723 (1977).

*Primary Examiner*—John M. Ford
*Attorney, Agent, or Firm*—Curtis, Morris & Safford

[57] ABSTRACT

Novel forskolin derivatives, intermediates and processes for the preparation thereof, and methods for treating cardiac failure and memory deficit utilizing compounds or compositions thereof are disclosed.

28 Claims, No Drawings

6- AND 7-DEOXYFORSKOLIN AND DERIVATIVES THEREOF

This application is a division of application Ser. No. 07/376,383, filed Jul. 6, 1989, now U.S. Pat. No. 5,093,336.

The present invention relates to forskolin derivatives and, in particular, to 6- and 7-deoxyforskolins. The forskolin derivatives of the invention are compounds of formula I

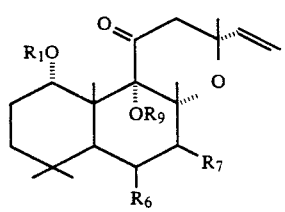

(I)

wherein
$R_1$ is hydrogen, loweralkyl, arylloweralkyl, a group of formula $R_2R_3R_4Si$, a group of formula $R_5CO$, a group of formula $R_8R_{10}N(CHR_{11})_nCO$ wherein n is 0 or 1, or Ar';

$R_6$ is hydrogen, hydroxyl, a group of formula $OR_{12}$, a group of formula $OCOR_{13}$, a group of formula $OCONR_{14}R_{15}$, or a group of formula OAr;

$R_7$ is defined as $R_6$, or is a group of formula $OCOR_{16}$, a group of formula $OCONR_{17}Z$, a group of formula OAr', a group of formula OCOAr', a group of formula $OCONR_{17}Ar$, or a group of formula

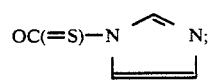

$R_6$ and $R_7$ taken together form a group of formula O—C(=S)—O;

$R_9$ is hydrogen;

$R_1$ and $R_9$ taken together form a group of formula CO, a group of formula SO or a group of formula $CHNR_{18}R_{19}$;

$R_2$, $R_3$, and $R_4$ are the same or not all the same and each is loweralkyl;

$R_5$ is hydrogen or loweralkyl;

$R_8$, $R_{10}$ and $R_{11}$ are the same or not all the same and each is hydrogen, loweralkyl or arylloweralkyl;

$R_8$ and $R_{10}$ taken together with the nitrogen atom to which they are attached form a group of formula

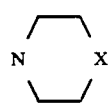

X is CO, O, S, a group of formula $CHR_{20}$ or a group of formula $NR_{21}$;

$R_{12}$ is loweralkyl or alkylaminoloweralkyl;

$R_{13}$ is hydrogen, straight or branched chain alkyl containing from 1 to 20 carbon atoms, —CH(OH)CH$_2$OH,

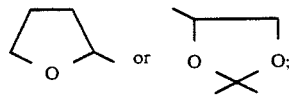

$R_{14}$ is hydrogen, loweralkyl, hydroxyloweralkyl, loweralkoxyloweralkyl, or a group of formula HOCH$_2$CH(OH)CH$_2$;

$R_{15}$ is hydrogen, hydroxyl, loweralkoxy, loweralkyl, hydroxyloweralkyl, loweralkoxyloweralkyl, loweralkanoyl, loweralkanoylloweralkyl, a group of formula

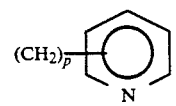

wherein p is 1 or 2, a group of formula

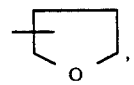

a group of formula HOCH$_2$(OH)CH$_2$, a group of formula $(CH_2)_qNR_{22}R_{23}$ wherein q is 0 or an integer from 2 to 6, a group of formula $OR_{24}$ or a group of formula $OCOR_{25}$;

$R_{16}$ is hydroxyloweralkyl,

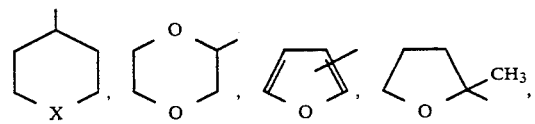

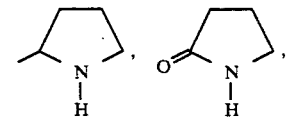

wherein X is as defined above, a group of formula $R_{26}OCR_{27}R_{28}(CH_2)_r$ wherein r is 0, 1, 2 or 3, a group of formula $R_{29}R_{30}N(CH_2)_s(CHR_{31})(CH_2)_{s'}$, wherein s and s' are the same or different and each is 0, 1 or 2 or a group of formula $(CH_2)_fCO_2H$, wherein f is an integer from 0 to 5;

$R_{17}$ is hydrogen or loweralkyl;

$R_{18}$ and $R_{19}$ are the same or different and each is loweralkyl;

$R_{18}$ and $R_{19}$ taken together with the nitrogen atom to which they are attached form a group of formula

wherein L is O, S or $CHR_{20}$;

$R_{20}$ is hydrogen or loweralkyl;

$R_{21}$ is hydrogen or loweralkyl;

$R_{22}$ and $R_{23}$ are the same or different and each is loweralkyl;

$R_{22}$ and $R_{23}$ taken together with the nitrogen atom to which they are attached form a group of formula

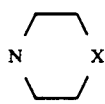

wherein X is defined as above;

$R_{24}$ is hydrogen, loweralkyl, a group of formula $(CH_2)_q NR_{22}R_{23}$ wherein $R_{22}$, $R_{23}$ and q are as above;

$R_{25}$ is hydrogen, loweralkyl, lowercycloalkyl of 3 to 6 carbon atoms, haloloweralkenyl, loweralkanoylloweralkyl, loweralkoxyloweralkyl, loweralkoxycarbonylloweralkyl, loweralkylamino, lowerdialkylamino, a group of formula

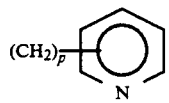

wherein p is defined as above, a group of formula

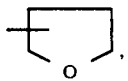

a group of the formula $(CH_2)_q NR_{22}R_{23}$ wherein $R_{22}$, $R_{23}$ and q are as defined above, a group of formula

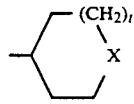

wherein X is as defined above and t is 0 or 1 or a group of formula $(CH_2)_u N(R_{33})COR_{34}$ wherein u is 1, 2 or 3;

$R_{26}$, $R_{27}$ and $R_{28}$ are the same or not all the same and each is hydrogen or loweralkyl;

$R_{29}$ is hydrogen, loweralkyl, or a group of formula $R_{35}CO$;

$R_{30}$ is hydrogen or loweralkyl;

$R_{29}$ and $R_{30}$ taken together with the nitrogen atom to which they are attached form a group of formula N

wherein X is defined above;

$R_{31}$ is hydrogen, loweralkyl, arylloweralkyl or hydroxyl;

$R_{33}$, $R_{34}$ and $R_{35}$ are the same or not all the same and each is hydrogen or loweralkyl;

Ar is phenyl, naphthyl, pyridinyl, pyridazinyl or pyrimidinyl, each of which is unsubstituted or mono- or poly-substituted by loweralkyl; halogen or nitro;

Ar' is aryl or substituted aryl including but not limited to furanyl, oxazolyl, pyridazinyl, purinyl or thiazolyl, each of which is unsubstituted or mono- or poly-substituted by loweralkyl, halogen, nitro, or a group of formula $NR_{34'}R_{35'}$, or phenyl, naphthyl, pyridinyl or pyrimidinyl, each of which is mono- or poly-substituted by a group of formula $NR_{34'}R_{35'}$;

$R_{34'}$ and $R_{35'}$ are the same or different and each is hydrogen, loweralkyl or alkylaminoloweralkyl;

$R_{34'}$ and $R_{35'}$ taken together with the nitrogen atom to which they are attached form a group of formula

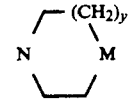

wherein M is $NR_{47'}$, O or $CH_2$ and y is 0, 1, or 2;

Z is a group of formula $(CH_2)_v NR_{37}R_{38}$ wherein v is 0 or an integer from 2 to 5, a group of formula $N=CR_{39}R_{40}$ or a group of formula $(CH_2)_g CO_2H$ wherein g is an integer from 0 to 5;

Z and $R_{17}$ and the nitrogen to which they are attached form a group

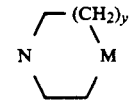

wherein M and y are defined as above;

$R_{37}$ and $R_{38}$ are the same or different and each is hydrogen, loweralkyl or a group of formula $COR_{41}$;

$R_{37}$ and $R_{38}$ taken together with the nitrogen atom to which they are attached form a group of formula

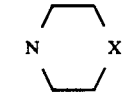

wherein X is defined as above;

$R_{39}$ is loweralkyl, $R_{40}$ is loweralkyl, loweralkenyl, a group of formula

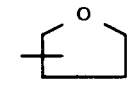

or a group of formula

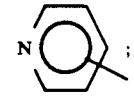

$R_{39}$ and $R_{40}$ taken together with the carbon atom to which they are attached form a group of formula

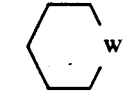

wherein W is O, a group of the formula $NR_{42}$, or a group of formula $CHR_{43}$;

$R_{41}$ is loweralkyl or a group of formula $(CH_2)_x NR_{44}R_{45}$ wherein x is an integer from 0 to 5;

$R_{42}$ is loweralkyl;

$R_{43}$ is hydrogen, loweralkyl or a group of formula $OR_{46}$;

$R_{44}$ and $R_{45}$ are the same or different and each is loweralkyl;

$R_{46}$ is loweralkyl;

$R_{47}$ is hydrogen, loweralkyl or (C=O) loweralkyl; and the optical and geometric isomers thereof, or a pharmaceutically acceptable salt thereof, provided:

(a) if $R_6$ is hydrogen, then $R_7$ is not hydrogen;
(b) if $R_7$ is hydrogen, then $R_6$ is not hydrogen; and
(c) if $R_6$ and $R_7$ are both not hydrogen, then R is OH, $R_{13}C(=O)O$, a group of formula $OR_{12}$, a group of formula $OCONR_{14}R_{15}$ or a group of formula OAr, $R_7$ is

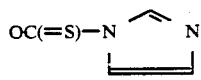

or $R_6$ and $R_7$ taken together form a group of formula O—C(=S)—O.

The present invention also relates to compounds of formula II

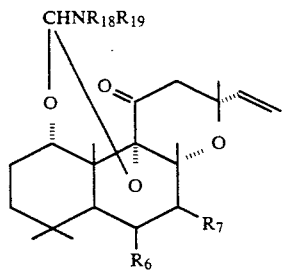

wherein $R_6$ is hydroxyl or $OCOR_{13}$, $R_7$ is

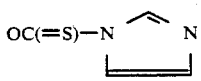

and $R_{13}$, $R_{18}$ and $R_{19}$ are as hereinbeforedefined, which are useful as intermediates in the preparation of the 6- and 7-deoxyforskolin derivatives of the present invention. In one embodiment, $R_{13}$, $R_{18}$ and $R_{19}$ are methyl.

Subgeneric to the forskolins of the present invention are compounds of formula I wherein:

$R_1$ is hydrogen;

$R_6$ is hydrogen, hydroxyl or $OCOR_{13}$;

$R_7$ is hydrogen, hydroxyl, $OCOR_{13}$, $OCONR_{14}R_{15}$, $OCOR_{16}$, a group of formula

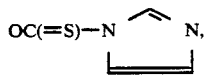

$OCONR_{17}(CH_2)_vNR_{37}R_{38}$ wherein v is an integer from 2 through 5, or $OAr^1$ wherein $Ar^1$ is phenyl, pyridinyl, pyridazinyl, pyrimidinyl, purinyl, each of which is unsubstituted or mono- or poly-substituted by loweralkyl, halogen, nitro, amino, substituted amino, aminoloweralkyl, piperazino, piperidino, or morpholino;

$R_9$ is hydrogen;

$R_1$ and $R_9$ taken together form a group of formula $CHNR_{18}R_{19}$; and $R_6$ and $R_7$ taken together form a group of formula O—C(=S)—O; and wherein $R_{12}$-$R_{19}$, $R_{37}$ and $R_{38}$ are as hereinbeforedefined.

As used throughout the specification and appended claims, the term "alkyl" refers to a straight or branched chain hydrocarbon radical containing no unsaturation and having 1 to 8 carbon atoms such as methyl, ethyl, 1-propyl, 2-propyl, 2-methylpropyl, 1-pentyl, 2-pentyl, 3-hexyl, 4-heptyl, 2-octyl, and the like. The term "alkenyl" refers to a straight or branched chain hydrocarbon radical containing one or more double bonds and having 1 to 8 carbon atoms such as propenyl, pentenyl, hexenyl, and the like. The term "alkanol" refers to a compound formed by a combination of an alkyl group and a hydroxyl radical and includes, for example, methanol, ethanol, 1- and 2-propanol, 1,2-dimethylethanol, hexanol, octanol, and the like. The term "alkoxy" refers to a compound formed by a combination of an alkyl group and an oxy group and includes, for example, methoxy, ethoxy, propoxy, butoxy, and the like. The term "alkoxide" refers to a compound formed by the combination of an alkoxy group and a metal and includes, for example, potassium t-butoxide. The term "alkanoic acid" refers to a compound formed by combination of a carboxyl group with a hydrogen atom or alkyl group. Examples of alkanoic acids are formic acid, acetic acid, propanoic acid, 2,2-dimethylacetic acid, hexanoic acid and the like. The term "acyl" refers to the radical derived from an alkanoic acid by removal of the hydroxyl group. The term "halogen" refers to a member of the family consisting of fluorine, chlorine, bromine or iodine. The term "lower" as applied to any of the aforementioned groups refers to a group having a carbon skeleton containing up to and including six carbon atoms. The term "hydroxyloweralkyl" refers to a straight or branched chain hydrocarbon radical of 1 to 6 carbon atoms containing no unsaturation which is mono- or polysubstituted by hydroxyl, such as hydroxymethyl, 1-hydroxyethyl, 1,2-dihydroxyethyl, 3-hydroxypropyl, 2,3-dihydroxypropyl, 4-hydroxybutyl, $CH_3C(CH_3)OH$, $HOCH_2C(CH_3)OH$, $HOCH_2C(CH_3)_2$, $HOC(CH_2OH)CH_2CH_3$, $CH_3C(CH_2OH)_2$ and the like. The term "substituted amino" refers to an amino radical which is mono- or disubstituted by loweralkyl such as methylamino, ethylamino, dimethylamino, diethylamino and the like. The term "aminoloweralkyl" refers to a loweralkyl radical which is mono- or polysubstituted by amino or substituted amino, such as 2-aminoethyl, 2-dimethylaminoethyl, 3-aminopropyl, 3-dimethylaminopropyl, 4-dimethylaminobutyl, and the like. The term "aryl" refers to an organic radical derived from an aromatic or heteroaromatic hydrocarbon by the removal of one hydrogen atom, such as, e.g., phenyl, tolyl, salicyl, naphthyl, pyridinyl, etc. The term "radical initiator" refers to an alkylazo compound such as 2,2'-azobis(2-methylpropionitrile).

In the formulas presented herein, the various substituents are illustrated as joined to the forskolin nucleus by one of two notations: a solid line (—) indicating a substituent which is in the β-orientation (i.e., above the plane of the molecule) an broken line (---) indicating a substituent which is in the α-orientation (i.e., below the plane of the molecule). The formulas have all been drawn to show the compounds in their absolute stereochemical configuration. Inasmuch as the starting materials having a forskolin nucleus are naturally occurring or are derived from naturally occurring materials, they, as well as the final products, have a forskolin nucleus existing in the single absolute configuration depicted herein. The processess of the present invention, however, are intended to apply as well to the synthesis of forskolins of the racemic series.

In addition to the optical centers of the forskolin nucleus, the substituents thereon may also contain chiral centers contributing to the optical properties of the compounds of the present invention and providing a means for the resolution thereof by conventional methods, for example, by the use of optically active acids. The present invention comprehends all optical isomers and racemic forms of the compounds of the present invention, where such compounds have chiral centers in addition to those of the labdane nucleus.

The novel forskolins of the present invention are synthesized by the representative processes illustrated in Schemes A and B.

Referring to Scheme A, compounds of formula 2 are prepared by reacting a compound of formula 1 (e.g., 7-desacetylforskolin-1,9-dimethylformamide acetal) with 1,1'- thiocarbonyldiimidazole to provide compound 2. Compound 2 is then treated with an organic or inorganic base to provide compound 3. Compound 3 is treated with a radical initiator, for example, 2,2'-azobis(2-methylpropionitrile) followed by a trialkyltin hydride, for example, tri-n-butyltin hydride, to provide compound 4. The dialkylformamide acetal of compound 4 is then hydrolyzed to provide 6-deoxy-7-desacetylforskolin, compound 5.

Derivatization of compound 1 at the 7-position to prepare compound 2 is readily accomplished by treating compound 1 with 1,1'-thiocarbonyldiimidazole in the presence of a pyridine catalyst, preferably an amino-substituted pyridine, e.g., 4-dimethylaminopyridine or 4-pyrrolidinopyridine. The reaction is conducted in a number of solvents well-known in the art. Of these solvents, tetrahydrofuran is preferred. While the temperature at which the reaction is performed is not narrowly critical, it is preferred to conduct the reaction at a temperature ranging from about 25° to 120° C. It is most preferred to perform the reaction at a temperature ranging from about 50° to 80° C. To prepare compound 3, ring formation at the 6- and 7- positions of compound 2 is achieved by treatment of compound 2 with an inorganic or organic base such as, e.g., sodium hydroxide, sodium carbonate or an alkali metal bis(trialkylsilyl)amide. Preferred bases include alkali metal bis(trialkylsilyl)amides, most preferably lithium bis(trimethylsilyl)amide. The reaction can be conducted in any of a number of solvents known in the art, preferably tetrahydrofuran.

Preparation of compound 4 is effected by modification of the method of Barton (D. H. R. Barton et. al., *J. Chem. Soc. Perkin I*, 1574-1585 (1975); ibid, 1718-1723 (1977)) which entails treatment of compound 3 with a radical initiator, preferably 2,2'-azobis(2-methylpropionitrile) followed by a trialkyltin hydride, preferably tri-n-butyltin hydride, in a solvent, preferably an aromatic solvent, most preferably toluene. While the temperature at which the reaction is performed is not narrowly critical, it is preferred to conduct the reaction at 90° to 130° C., more preferably at 100° to 115° C.

Compound 4 can be 0-acylated in the 7-position, yielding compound 6 wherein $R_7$ is acyl, by treating compound 4 with a carboxylic acid anhydride of formula $R_{13}$—C($=$O)—O—C($=$O)—$R_{13}$ or a mixed anhydride of formula $R_{13}$—C($=$O)—O—C($=$O)—H, wherein $R_{13}$ is hereinbeforedefined, or a suitably protected derivative thereof, in the presence of a 4-substituted aminopyridine in a suitable solvent. An example of a suitable carboxylic acid anhydride is acetic anhydride, an example of a suitable 4-substituted aminopyridine is 4-N,N-dimethylaminopyridine and an example of a suitable solvent is methylene chloride. The acylation reaction is carried out at a temperature ranging from about 0° to 50° C., preferably at room temperature.

Similarly, compounds 7 wherein $R_7$ is $COR_{16}$, wherein $R_{16}$ is as hereinbeforedescribed, can be prepared by treating compound 5 with an organic acid of formula $R_{16}CO_2H$ in a halocarbon such as dichloromethane or chloroform in the presence of a carbodiimide such as dicyclohexylcarbodiimide or 1-(3-dimethylaminopropyl)-3-ethylcarbodiimide and a catalyst such as 4-(N,N-dimethylamino)pyridine or 4-(pyrrolidino)pyridine at a reaction temperature within the range of about 0° to about 50° C. Dichloromethane is the preferred solvent. A reaction temperature of about 25° C. is also preferred.

To prepare a compound 7 wherein $R_7$ is a dihydroxyalkanoyl group, a compound 7 wherein $R_7$ is dioxolanoyl is cleaved to afford the desired dihydroxyalkanoyl derivative. The cleavage is accomplished by contacting the dioxolanoyl-forskolin 7 with an aqueous alkanoic acid in an alkanol. Among alkanoic acids, there may be mentioned acetic acid, propionic acid, and the like. Among alkanols there may be mentioned methanol, ethanol, 1- and 2-propanol, t-butanol and the like. Aqueous acetic acid/methanol is preferred. While the cleavage proceeds readily at a reaction temperature within the range of about 25° to about 85° C., a reaction temperature within the range of about 50° to 70° C. is preferred.

Compounds 6 wherein $R_7$ is $COHNR_{15}$ or $R_7$ is $CONR_{14}R_{15}$ can be prepared by treating compound 4 with a base, for example, an alkali metal bis(triloweralkylsilyl)amide in an organic solvent, such as, for example, an ethereal solvent, to form an alkali metal alkoxide of compound 4 which is then treated with either an isocyanate of formula $R_{15}NCO$ (or a suitably protected derivative thereof) or a carbamoyl halide of formula $HalCONR_{14}R_{15}$, neat or in an ethereal solution. Examples of alkali metal bis(triloweralkylsilyl)amides include lithium, sodium or potassium bis(trimethylsilyl)- or bis(triethylsilyl)amides and the like. Examples of ethereal solvents are diethyl ether, 1,2-dimethoxyethane, dioxane, tetrahydrofuran and the like. A reaction medium consisting of lithium bis(triethylsilyl)amide and tetrahydrofuran is preferred. The formation of the alkali metal alkoxide is performed within the non-critical range of about $-25°$ C. to about 50° C., preferably a temperature of about 0° C. to about 25° C. The condensation of an alkali metal alkoxide of compound 4 with the aforementioned isocyanate or carbamoyl halide is performed at a temperature of about 0° C. to about the reflux temperature of the reaction medium, preferably at about 25° C. to the reflux temperature.

To prepare a compound 6 wherein $R_7$ is $CONR_{14}R_{15}$ or $CONR_{17}(CH_2)_vNR_{37}R_{38}$, compound 4 is treated with a phosgene equivalent, preferably 1,1'-carbonyldiimidazole, in an alkyl alkanoate or a halocarbon. The resulting acylated compound is then treated with an amine of formula $HNR_{14}R_{15}$ or an amine of formula $HNR_{17}(CH_2)_\nu NR_{37}R_{38}$, neat, in an alkyl alkanoate, halocarbon or a mixture of a halocarbon and an alkanol to yield the respective compounds 6. Among alkyl alkanoates there may be mentioned ethyl acetate, ethyl propionate and the like.. Ethyl acetate is preferred. Among halocarbons there may be mentioned dichloromethane, chloroform and the like. Dichloromethane is preferred. Among alkanols there may be mentioned methanol, ethanol, 2-propanol and the like. Methanol is preferred and mixtures of dichloromethane and methanol are also preferred. Dichloromethane is most preferred. While the temperature at which the reaction is performed is not narrowly critical, it is preferred to carry out the reaction at a temperature from about 0° C. to the reflux temperature of the solvent system, most preferably at a temperature of about 25° C.

If desired, the intermediate acylated compound may be isolated by workup of the reaction mixture prior to the addition of amine by methods well-known in the art. For example, the intermediate acylated compound may be isolated by chromatography on a suitable column (e.g., silica gel) with an appropriate eluent such as hexane/ethyl acetate.

Aryl ethers at the 7-position of compound 4 can be readily obtained by treating compound 4 with an aryl- or heteroaryl halide in the presence of a metal alkoxide or metal bis(trialkylsilylamide). Aryl- or hetereoaryl halides used in accordance with the invention have the formula Ar-Hal, wherein Ar is phenyl, naphthyl, pyridinyl, pyrimidinyl, furanyl, oxazolyl, pyridazinyl, thiazolyl or purinyl, each of which is unsubstituted or mono- or polysubstituted by loweralkyl, halogen or nitro and Hal is halogen, and include, for example, 2-fluoropyridine, 2-chloropyrimidine, 2,6-difluoropyridine, 1-fluoro-4-nitrobenzene, 2,4-dinitrofluorobenzene, 2,4-dichloropyrimidine and 6-chloro-1-methyl-purine. The arylation is conducted in a number of solvents well known in the art. Of these solvents, tetrahydrofuran is preferred. Metal alkoxides used in accordance with the invention include a number of substances well known in the art, potassium t-butoxide being preferred and a metal bis(trialkylsilylamide), e.g., potassium bis(trimethylsilylamide), being most preferred. While the temperature at which the arylation is performed is not narrowly critical, it is preferred to conduct the reaction at a temperature ranging from about $-20°$ to 100° C. It is most preferred to perform the arylation at a temperature ranging from about 0° to 50° C.

To obtain an aryl ether at the 7-position of compound 6 wherein the aryl group (i.e., $R_7$) is mono- or polysubstituted by amino, substituted amino or aminoloweralkyl, an aryl ether of compound 6 wherein the aryl group is mono- or polysubstituted by halogen is treated with an amine compound of formula $HNR_{34'}R_{35'}$, preferably in the presence of a mineral acid, wherein $R_{34'}$ and $R_{35'}$ are the same or different and each is hydrogen, loweralkyl or aminoloweralkyl and $R_{34'}$ and $R_{35'}$ taken together with the nitrogen atom to which they are attached form a group of formula

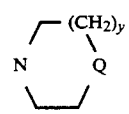

wherein Q is $NR_{48}$, wherein $R_{48}$ is loweralkyl, (C=O)-loweralkyl or (C=O)Ophenyl, O or $CH_2$ and y is 0, 1 or 2. Compounds of formula $HNR_{34'}R_{35'}$ include, for example, anhydrous ammonia, 3-dimethylaminopropylamine, 2-dimethylaminoethylamine, methylamine, ethylamine, dimethylamine, diethylamine, morpholine,

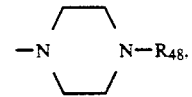

piperidine, and the like. Mineral acids include hydrochloric acid and sulfuric acid. While the temperature at which the reaction is performed is not narrowly critical, it is preferred to conduct the reaction at temperature ranging from about 75° C. to about 160° C. Higher boiling amines, e.g., morpholine,

and piperidine can be used as the solvent. For more volatile amines, a solvent, such as toluene, can be used and the reaction is conducted in a sealed vessel.

Ethers at the 7-position of compound 6, i.e., wherein $R_7$ is loweralkyl or alkylaminoloweralkyl, may be obtained by derivatizing compound 4 using methods known in the art for preparing ethers, such as, treatment with a diazoalkane in the presence of a catalyst or treatment of the potassium or sodium alkoxide of 4 with the appropriate alkyl halide (Williamson Synthesis).

Referring now to Scheme B, to prepare 7-deoxyforskolin compound 10, compound 8 is reacted with a trialkyltin hydride, preferably tri-n-butyltin hydride in a solvent, preferably an aromatic solvent, most preferably toluene, to afford compound 9. A radical initiator, for example, 2,2'-azobis(2-methyl-propionitrile), while not always necessary, can be used with trialkyltin hydride. The reaction is conducted at a temperature ranging from about 90° to about 130° C., preferably about 100° C. to about 115° C. The resulting 7-desacetoxyforskolin-1,9-dialkylformamide acetal 9 is deacetalated to afford compound 10.

To obtain a 7-deoxyforskolin which is acylated in the 6-position, compound 11 wherein $R_6$ is acyl is treated with a compound of formula

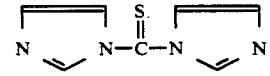

in a manner analogous to the preparation of compound 2 shown in Scheme A, but preferably at a temperature ranging from about 90° C. to 120° C., to afford compound 12. Compound 12 is then reacted, as previously described in the preparation of compound 9, to afford the 7-desacetoxyforskolin-1,9-dialkyl-formamide acetal 13. Compound 13 is then deacetalated to afford compound 14.

Compounds 14 wherein A is $COR_{13}$, $CONR_{14}R_{15}$, $CONR_{17}(CH_2)_\nu NR_{36}R_{37}$ or Ar may be prepared from compounds 9 and/or 10 using methods analogous to those described above and used to prepare compounds 7, wherein $R_7$ has the same meanings, from compounds 4 and/or 5.

Deacetalation of compounds 4, 6, 9 and 13 is effected by hydrolysis with a mixture of an alkanol and water, a mixture of alkanol, water and an alkanoic acid or a mixture of a mineral acid, an alkanol and water. Included among alkanoic acids are formic acid, acetic acid, propionic acid and the like. Included among mineral acids are hydrochloric acid, sulfuric acid and the like. Included among alkanols are methanol, ethanol, 2-propanol and the like. A reaction medium consisting of about 80% aqueous acetic acid and methanol or aqueous methanol is preferred. The hydrolysis proceeds readily at a temperature within the range of about 0° C. to about 50° C. in 80% aqueous acetic acid, and about 40° C. to 90° C. in aqueous methanol. The preferred hydrolysis temperatures in aqueous acetic acid and aqueous methanol are about 25° and 65° C., respectively.

The forskolin starting materials represented by compound 1 in Scheme A and compound 11 in Scheme B are described in U.S. Pat. Nos. 4,134,986, 4,639,443 and 4,677,103, issued Jan. 16, 1979, Jan. 27, 1987 and Jun. 30, 1987, respectively, the disclosures of which are incorporated herein by reference, or may be prepared from compounds disclosed therein by conventional methods.

U.S. Pat. No. 4,639,446, issued Jan. 27, 1987, U.S. Pat. No. 4,666,904, issued May 19, 1987, U.S. Pat. No. 4,672,115, issued Jun. 9, 1987 and U.S. Pat. No. 4,673,752, issued Jun. 16, 1987, the disclosure of each of which patents is incorporated herein by reference, as well as U.S. Pat. Nos. 4,134,986, 4,639,443 and 4,677,103 disclose a variety of methods which can be used for further derivatization of forskolin compounds 4 and 5 of the present invention at the 1- and 7-positions and forskolin compounds 9 and 10 at the 1- and 6-positions. U.S. application Ser. No. 137,998, filed Dec. 28, 1987, also discloses methods which can be used for further derivatization of these compounds at the 1-, 6- and 7-positions. In particular, these methods can be used to prepare compounds of the invention wherein $R_1$ is $R_2R_3R_4Si$, $R_5CO$ and $R_8R_{10}N(CHR_{11})_nCO$ wherein $R_2$, $R_3$, $R_4$, $R_5$, $R_8$, $R_{10}$, $R_{11}$ and n are hereinbeforedefined. S. V. Bhat et al., "The Antihypertensive and Positive Inotropic Diterpene Forskolin: Effects of Structural Modifications on Its Activity", J. Med. Chem., 26, 487–493 (1983) and S. V. Bhat et al., "Reactions of Forskolin, A Biologically Active Diterpenoid from *Coleus forskolii*", J. Chem. Soc., Perkin I, 767–771 (1982) disclose methods which can be used for derivatization of compounds 5, 7, 10 and 14 of the present invention at the 1-position wherein $R_1$ is loweralkyl or aryloweralkyl. U.S. Ser. No. 191,457, filed May 9, 1988, discloses methods which may be used to prepare compounds 6 wherein $R_7$ is $OCONR_{17}NR_{37}R_{38}$ or $OCONR_{17}N=CR_{39}R_{40}$.

The forskolin derivatives of the present invention are useful in the treatment of cardiac failure by virtue of their ability to elicit a positive inotropic effect as determined in the isolated guinea pig atria contractile force assay. The electrically-driven guinea pig left atrium assay is performed as follows:

Male guinea pigs weighing 200–300 grams are stunned with a blow to the back of the head. The heart is rapidly removed and placed in a petri dish containing Krebs solution. The ventricle is separated from the atria, the atria are sectioned in the right and left atria, and double-O silk ligatures are tied to the apex of the left atrium. The atrium is fixed to a pair of platinum plate electrodes and suspended in a 20-ml tissue bath containing Kreb's solution aerated with 95% oxygen-5% carbon dioxide at 37° C. One end of the atrium is fixed to a hook in the electrode and the other end is connected to a Grass FTO3 force displacement transducer. Resting tension and stabilization time are the same as described above. The atrium is stimulated at 3 Hz, 0.5 msec duration at supramaximal voltage (constant current) via a Grass S88 stimulator and constant current unit. Force of contraction is continuously displaced on a Gould recorder. Test drug is prepared and is added to the tissue baths. Change in contractile force from baseline is determined for each concentration, and the change in contractile force (g) is plotted against accumulated drug concentration ($\mu g/ml$) The activity of the test drug, i.e., the increase in contractile force (g) from the stabilized force expressed as the percentage change at a given concentration is determined graphically, as is the $ED_{50}$-value, i.e., the extrapolated dose ($\mu g/ml$) which increases the contractile force by 50% over the stabilized rate.

Results obtained in this assay for representative compounds of the invention and a reference compound are presented in the Table.

TABLE

| Compound | Concentration ($\mu g/ml$) | Ionotropic Activity (% Change of Contractile Force) |
|---|---|---|
| A[1] | 0.04[2] | 50 |
| B[3,4] | 0.073[2] | 50 |

[1] 6-Deoxy-7-desacetyl-7(pyrimidin-2-yl)forskolin hydrochloride
[2] Extrapolated $ED_{50}$ value
[3] Forskolin
[4] Reference Compound Cardiac failure treatment is achieved when the forskolin derivatives of the present invention are administered to a subject requiring such treatment as an effective oral, parenteral or intravenous dose of from about 0.01 to 100 mg/kg of body weight per day. A particularly effective amount is about 25 mg/kg of body weight per day. It is to be understood, however,.that for any particular subject, specific dosage regimens should be adjusted according to the individual need and the professional judgment of the person administering or supervising the administration of the aforesaid compound. It is to be further understood that the dosage set forth herein are exemplary only and that they do not, to any extent, limit the scope of practice of the invention.

Compounds of the present invention are also useful for the treatment of hypertension, memory deficit, senile dementia of the Alzheimers type, bronchial asthma, glaucoma and psoriasis.

Compounds of the present invention include:

6-deoxy-7-desacetyl-7-(2-dimethylaminoethylaminocarbonyl)forskolin;

6-deoxy-7-desacetyl-7-(2-dimethylaminoethyl)forskolin;

6-deoxy-7-desacetyl-7-(3-dimethylaminopropyl)forskolin;

6-deoxy-7-desacetyl-7-[2-(3-dimethylaminopropylamino)pyrimidin-4-yl]forskolin;

6-deoxy-7-desacetyl-7-[2-(2-dimethylaminoethylamino)pyrimidin-4-yl]forskolin;

6-deoxy-7-desacetyl-7-(1-methylpurin-6-yl)forskolin;

6-deoxy-7-desacetyl-7-(2-aminoethylaminocarbonyl)forskolin;

6-deoxy-7-desacetyl-7-(3-aminopropylaminocarbonyl)forskolin;

6-deoxy-7-desacetyl-7-[2-hydroxyethylaminocarbonyl)-forskolin;

6-deoxy-7-desacetyl-7-(3-hydroxypropyl-aminocarbonyl)forskolin;

7-desacetoxy-6-(3-dimethylaminopropylaminocarbonyl)PL-forskolin;

7-desacetoxy-6-(2-dimethylaminoethylaminocarbonyl)-forskolin;

7-desacetoxy-6-(methylaminocarbonyl)forskolin;

7-desacetoxy-6-(3,4-dinitrophenyl)forskolin;

6-deoxy-7-desacetyl-7-(2,3-dihydroxypropionyl)forskolin;

6-deoxy-7-desacetyl-7-(3-hydroxypropionyl)forskolin;

6-deoxy-7-desacetyl-7-y(3-dimethylaminopropionyl)-forskolin;

6-deoxy-7-desacetyl-7-(4-dimethylaminobutyryl)forskolin;

6-deoxy-7-desacetyl-7-(dimethylaminoacetyl)forskolin;

6-deoxy-7-desacetyl-7-(aminoacetyl)forskolin;

6-deoxy-7-desacetyl-7-(3-aminopropionyl)forskolin; and 6-deoxy-7-desacetyl-7-[6-(3-dimethylaminopropyl)pyridine-2-yl]forskolin;

Effective quantities of the compounds of the invention may be administered to a patient by any of the various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0-300 milligrams of active compound.

The tablets, pills, capsules, troches and the like may also contain the following ingredients: a binder such as micro-crystalline cellulose, gum tragacanth or gelatin; an excipient such as starch or lactose a disintegrating agent such as alginic acid, Primogel ®, corn starch and the like; a lubricant such as magnesium stearate or Sterotex ®; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to material of the above type, a liquid carrier such as a fatty oil. Other dosage unit forms may contain other various materials which modify the physical form of the dosage unit, such as, for example, coatings. Thus tablets or pills may be coated with sugar, shellac or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 5% of the weight thereof. The amount of active compound in such compositions is such that a suitable dosage will be obtained. Preferred compositions and preparations according to the present inventions are prepared so that a parenteral dosage unit contains between 0.001 to 10 milligrams of active compound.

The solutions or suspensions may also include the following components: a sterile diluent such as water for injection, saline solution, fixed oils, polyethylene glycols, glycerine, propylene glycol or other synthetic solvents antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparations can be enclosed in disposable syringes or multiple dose vials made of glass or plastic.

The following examples are for illustrative purposes only in order to better understand the invention. All temperatures are given in degrees Centigrade.

EXAMPLE 1

Preparation of 7-Desacetyl-7-(imidazolothiocarbonyl) for-skolin- 1,9-dimethylformamide acetal To a stirred solution of 5.0 g (11.8 mmol) of 7-desacetylforskolin-1,9-dimethylformamide acetal in 75 ml tetrahydrofuran was added 2.5 g (14.0 mmol) of 1,1'-thiocarbonyldiimidazole. The solution was stirred at room temperature for 16 hr. To the solution was added 150 mg of 4-dimethylaminopyridine after which the solution was stirred at reflux for 3 hr. The solution was allowed to cool to room temperature and 1.0 g (5.6 mmol) of 1,1'-thiocarbonyldiimidazole was added. The mixture was stirred at reflux for 4 hr, allowed to cool to room temperature and concentrated to an oil. The oil was purified by flash chromatography on silica gel, eluting with 15% ethyl acetate/hexane followed by 20% and subsequently 25% ethyl acetate/hexane. The product-containing fractions were combined and concentrated to provide an oil which crystallized on standing. The material was recrystallized from ether/hexane to provide, after drying at 80° (2 mm), 4.17 g (66.2%) of 7-desacetyl-7-(imidazolothiocarbonyl)forskolin-1,9-dimethylformamide acetal, mp 200°-202° C. The material appeared pure by thin layer chromatography on silica gel: 1/1 acetone/hexane, $R_f$=0.6; 1/1 ethyl acetate/hexane, $R_f$=0.4. IR(CHCl$_3$), NMR(CDCl$_3$) and mass spectra (MH$^+$=534) were consistent with the assigned structure.

ANALYSIS: Calculated for $C_{27}H_{39}N_3O_6S$: 60.77%C 7.37%H 7.87%N; Found: 61.24%C 7.46%H 7.87%N.

EXAMPLE 2

Preparation of 7-Desacetoxy-7(H)forskolin-1,9-dimethylformamide acetal

To a stirred solution of 200 mg (0.375 mmol) of 7-desacetyl-7-(imidazolothiocarbonyl)forskolin-1,9-dimethylformamide acetal (prepared as described in Example 1) and 9 mg (0.055 mmol) of 2,2'-azobis(2-methylpropionitrile) in 10 ml of dry toluene under nitrogen was added 0.71 ml (0.767 g, 2.64 mmol) of tributyltin hydride. The solution was warmed to 60° over 0.5 hr and to 115° C. over the subsequent 0.5 hr. The solution was allowed to cool to room temperature, concentrated to an oil under high vacuum and flash chromatographed on silica gel. The column was eluted with 15% ethyl acetate/hexane followed by 20% ethyl acetate/hexane. The pure product-containing fractions were combined and concentrated to provide an oil which crystallized on standing. Recrystallization from cyclohexane provided 38.4 mg (0.0941 mmol; 25.1%) of 7-desacetoxyforskolin-1,9-dimethylformamide acetal, mp 158°–160° C. The material appeared pure by thin layer chromatography on silica gel: 30% ethyl acetate/hexane, $R_f=0.3$; 2/1 hexane/ethyl acetate, $R_f=0.5$, IR(CHCl$_3$), NMR(CDCl$_3$) and mass spectra (MH+ =408) were consistent with the assigned structure.

ANALYSIS Calculated for $C_{23}H_{37}NO_5$: 67.78%C 9.15%H 3.44%N; Found: 67.80%C 8.99%H 3.37%N.

EXAMPLE 3

Preparation of 7-Desacetylforskolin-1,9-dimethylformamide-acetal-6,7-thionocarbonate To a stirred solution of 2.0 g (3.74 mmol) of 7-desacetyl-7-(imidazolothiocarbonyl)forskolin-1,9-dimethylformamide acetal (prepared as described in Example 1) in 140 ml of dry tetrahydrofuran in an ice bath was added dropwise 0.4 ml of 1M lithium bis(trimethylsilyl)amide in tetrahydrofuran. The solution was stirred 3 hr at 0° C. and allowed to warm to room temperature. The mixture was again cooled to 0° C., poured into ice/ammonium chloride/ethyl acetate, extracted with cold ethyl acetate, and the extracts were combined, washed with cold water, saturated sodium chloride and dried over sodium sulfate. Filtration followed by evaporation of solvent provided an oil which crystallized on standing. The material was purified by flash chromatography on silica gel, eluting with 15% ethyl acetate/hexanes followed by 20% ethyl acetate/hexanes. The pure, product-containing fractions were combined and concentrated to provide an oil which crystallized on standing. The material was recrystallized from cyclohexane to provide 1.69 g (3.62 mmol, 96.8%) of 7-desacetylforskolin-1,9-dimethylformamide acetal-6,7-thionocarbonate, mp 158°–160° C. The material appeared pure by thin layer chromatography on silica gel: 20% ethyl acetate/hexanes, $R_f=0.16$; 2/1 acetone/hexane, $R_f=0.5$. IR(CHCl$_3$), NMR(CDCl$_3$) and mass spectra (MH+ =466) were consistent with the assigned structure.

ANALYSIS Calculated for $C_{24}H_{35}NO_6S$: 61.91%C 7.58%H 3.01%N; Found: 61.77%C 7.46%H 2.80%N.

EXAMPLE 4

Preparation of 6-Deoxy-7-desacetoxy-7-hydroxyforskalin-1,9-dimethylformamide acetal To a stirred solution of 1.0 g (2.14 mmol) of 7-desacetylforskolin-1,9-dimethylformamide acetal-6,7-thionocarbonate (prepared as described in Example 3) and 50 mg (0.305 mmol) of 2,2'-azobis(2-methylpropionitrile) in 60 ml dry toluene was added 4.0 ml (26.3 mmol) of tributyltin hydride. The solution was heated to 110° and stirred at 100°–110° C., under nitrogen, for 1.5 hr. The solution was allowed to cool to room temperature and concentrated to an oil which was purified by flash chromatography on silica gel, eluting with 15% ethyl acetate/hexanes, followed by 20% ethyl acetate/hexanes. The pure, product-containing fractions were combined and concentrated to provide an oil which crystallized on standing to give 0.328 g (0.806 mmol, 37.7%) of 6-deoxy-7-desacetylforskolin-1,9-dimethylformamide acetal. The material was recrystallized from hexane to provide 0.235 g, mp 106°–110° C. The material appeared pure by thin layer chromatography of silica gel: 15% ethyl acetate/hexanes, $R_f=0.12$; 30% acetone hexanes, $R_f=0.38$. IR(CHCl$_3$), NMR(CDCl$_3$) and mass spectra (MH+ =408) were consistent with the assigned structure.

ANALYSIS: Calculated for $C_{23}H_{37}NO_5$: 67.78%C 9.15%H 3.44%N; Found: 68.14%C 9.06%H 3.50%N.

EXAMPLE 5

Preparation of 7-Desacetoxy-7(H)forskolin

A stirred solution of 178 mg (0.436 mmol) of 7-desacetoxyforskolin 1,9-dimethylformamide acetal (prepared as described in Example 2) in 10 ml of methanol and 2 ml of water was stirred for 16 hr at 68° C. and for 24 hr in a sealed tube at 80°–85° C. The solution was allowed to cool to room temperature and concentrated to a white solid. The material was purified by flash chromatography on silica gel, eluting with 15% ethyl acetate/hexanes. The pure fractions were combined and concentrated to provide a white solid which was recrystallized from ethyl acetate/hexane to provide 53 mg (0.13 mmol, 29.8%) of 7-desacetoxyforskolin, mp 194°–198° C. The material appeared pure by thin layer chromatography on silica gel: 20% ethyl acetate/hexanes, $R_f=0.15$; 30% acetone/hexanes, $R_f=0.30$. IR(CHCl$_3$), NMR(CDCl$_3$) and mass spectra (M+ −18=334) were consistent with the assigned structure.

ANALYSIS: Calculated for $C_{20}H_{32}O_5$: 68.15%C 9.15%H; Found: 68.21%C 9.09%H.

EXAMPLE 6

Preparation of 6-Deoxy-7-desacetoxy-7-hydroxyforskalin

A solution of 0.475 g (1.17 mmol) of 6-deoxy-7-desacetylforskolin-1,9-dimethylformamide acetal (prepared as described in Example 4) in 25 ml of methanol and 8 ml of water was stirred at 70° C. overnight. The solution was allowed to cool to room temperature and then concentrated to an oil which crystallized on standing. The material was purified by flash chromatography on silica gel, eluting with 15% ethyl acetate/hexanes followed by 20% ethyl acetate hexanes. The pure product-containing fractions were combined and concentrated to provide 0.285 g (0.809 mmol, 69.1%) of a solid which was recrystallized from ethyl acetate to provide 6-deoxy-7-desacetylforskolin, mp 192°–196° C. The solid appeared pure by thin layer chromatography on silica gel: 20% ethyl acetate/hexanes, $R_f$=0.14; 2% methanol/dichloromethane, $R_f$=0.13. IR(CHCl$_3$), NMR(CDCl$_3$) and mass spectra (MH+ =352) were consistent with the assigned structure.

ANALYSIS: Calculated for C$_{20}$H$_{32}$O$_5$: 68.15%C 9.15%H; Found: 68.14%C 9.01%H.

EXAMPLE 7

Preparation of 6-Deoxyforskolin-1,9-dimethylformamide acetal

To 2.00 g (4.91 mmol) of 6-deoxy-7-desacetylforskolin-1,9-dimethylformamide acetal (prepared as described in Example 4) in 42 ml of methylene chloride was added 0.56 ml (5.9 mmol) of acetic anhydride and 0.06g (0.49 mmol) of 4-dimethylaminopyridine. The solution was stirred for 2 hr at room temperature under nitrogen, after which an additional 0.54 g (4.5 mmol) of 4-dimethylaminopyridine was added. The solution was stirred for an additional 2.5 hr under nitrogen and was then concentrated. The residue was purified by flash chromatography, eluting with 30% ethyl acetate/hexane and the product-containing fractions were combined and concentrated. The residue was dried at 110° C. for 4 hr to provide 2.06 g (4.58 mmol, 93%) of 6-deoxyforskolin-1,9-dimethylformamide acetal, mp 100°–102°. The material appeared pure by thin layer chromatography on silica gel: 30% ethyl acetate/hexane, $R_f$=0.31; 10% methanol methylene chloride, $R_f$=0.70. NMR (CDCl$_3$, D$_2$O), IR(CHCl$_3$) and mass spectra (MH+ =450) were consistent with the assigned structure.

ANALYSIS: Calculated for C$_{25}$H$_{39}$NO$_6$: 66.79%C 8.74%H 3.12%N; Found: 66.88%C 8.73%H 3.05%N.

EXAMPLE 8

Preparation of 6-Deoxy-7-desacetyl-7-(pyrimidin-2-yl)-forskolin-1,9-dimethylformamide acetal To 2.15 g (5.29 mmol) of 6-deoxy-7-desacetylforskolin-1,9-dimethylformamide acetal (prepared as described in Example 4) in 40 ml of dry tetrahydrofuran was added 0.591 g (5.27 mmol) of potassium t-butoxide. The suspension was stirred for several minutes, after which 0.727 g (6.35 mmol) of 2-chloropyrimidine was added. The reaction mixture was stirred at room temperature under nitrogen for 1 hr, poured into a mixture of ice/water/methylene chloride, extracted with methylene chloride, and the extracts were washed with saturated sodium chloride, dried over sodium sulfate, filtered and concentrated. The resulting oil was purified by flash chromatography, eluting with 25% ethyl acetate/hexane and the product-containing fractions were combined and concentrated. The residue was dried at 110° C. for 5½ hr to provide 1.28 g (2.67 mmol, 50%) of 6-deoxy-7-desacetyl-7-(pyrimidin-2-yl)forskolin-1,9-dimethylformamide acetal, mp 108°–110° C. The material appeared pure by this layer chromatography on silica gel: 1/1 ethyl acetate/hexane, $R_f$=0.50; 10% methanol, methylene chloride, $R_f$=0.62. NMR(CDCl$_3$, D$_2$O), IR(CHCl$_3$) and mass spectra (MH+ =486) are consistent with the assigned structure.

ANALYSIS: Calculated for C$_{27}$H$_{39}$N$_3$O$_5$: 66.78%C 8.09%H 8.65%N; Found: 67 10%C 8.18%H 8.64%N.

EXAMPLE 9

Preparation of 6-Deoxyforskolin

To 1.67 g (3.71 mmol) of 6-deoxyforskolin-1,9-dimethylformamide acetal (prepared as described in Example 7) was added 82 ml of a 3:1 mixture of methanol/water. The solution was stirred under nitrogen at 60°–70° C. for 6 hr, and subsequently at 10° C. for 96 hr. The solution was concentrated and the residue purified by flash chromatography, eluting with 20% ethyl acetate/hexane. The product-containing fractions were combined and concentrated to a crystalline solid. Recrystallization from ethyl acetate/hexane provided 0.845 g (2.14 mmol, 58%) of a solid which was again recrystallized from ethyl acetate/hexane to give 6-deoxyforskolin, mp 191°–193° C. The material appeared pure by thin layer chromatography on silica gel: 1/1 ethyl acetate/hexane, $R_f$=0.58; 10% methanol/methylene chloride, $R_f$=0.68. NMR(CDCl$_3$, D$_2$O ), IR(CHCl$_3$), and mass spectra (M+ =394) are consistent with the assigned structure.

ANALYSIS: Calculated for C$_{22}$H$_{34}$O$_6$: 66.98%C 8.69%H; Found: 66.93%C 8.62%H.

EXAMPLE 10

Preparation of 6-Deoxy-7-desacetyl-7-(pyridin-2-yl)-forskolin-1,9-dimethylformamide acetal To a solution of 1.93 g (4.75 mmol) of 6-deoxy-7-desacetylforskolin-1,9-dimethylformamide acetal (prepared as described in Example 4) in 40 ml dry tetrahydrofuran was added 0.533 g (4.75 mmol) of potassium t-butoxide, followed by 0.49 ml (5.69 mmol) of 2-fluoropyridine. The reaction mixture was stirred for an additional 2 hr after which it was poured into a mixture of ice/water/methylene chloride, extracted with methylene chloride, and the extracts were combined, washed with saturated sodium chloride, dried over sodium sulfate, filtered and concentrated. The resulting oil was purified by flash chromatography on silica gel, eluting with 20% ethyl acetate/hexane. The product-containing fractions were combined and concentrated. The residue was dried at 100° C. for 5 hr to provide 0.538 g (1.11 mmol, 23%) of 6-deoxy-7-desacetyl-7-(pyridin-2-yl)forskolin 1,9-dimethyl-formamide acetal, mp 84°–87° C. The material appeared pure by thin layer chromatography on silica gel: 25% ethyl acetate/hexane, $R_f$=0.27; 10% methanol/methylene chloride, $R_f$=0.72. NMR(CDCl$_3$), IR(CHCl$_3$), and mass spectra (MH+ =485) were consistent with the assigned structure.

ANALYSIS: Calculated for C$_{28}$H$_{40}$N$_2$O$_5$: 69.39%C 8.32%H 5.78%N; Found: 69.57%C 8.20%H 5.69%N.

EXAMPLE 11

Preparation of 6-Deoxy-7-desacetyl-7-(pyrimidin-2-yl)forskolin hydrochloride

To 0.638 g (1.31 mmol) of 6-deoxy-7-desacetyl-7-(pyrimidin-2-yl)forskolin-1,9-dimethylformamide acetal (prepared as described in Example 8) was added 31 ml of a 3:1 mixture of methanol/water. The solution was stirred under nitrogen at 60°–70° for 6 hr. The solution was concentrated and the residue purified by flash chromatography on silica gel, eluting with 20% ethyl acetate/hexane. The product-containing fractions were combined and concentrated to a solid. Recrystallization of the solid from ethyl acetate/hexane provided 0.378 g (0.876 mmol) of a white solid which was dried at 110° C. for 2 hr. The dried white solid was dissolved in ether, ethereal hydrogen chloride was added and the white precipitate was collected by filtration and dried at 80° C. for 2 hr to provide 0.367 g (0.787 mmol, 60%) of 6-deoxy-7-desacetyl- 7-(pyrimidin-2-yl)forskolin hydrochloride, mp 177°–178° C. (dec.). The free base (regenerated from methylene chloride/sodium bicarbonate) appeared pure by thin layer chromatography on silica gel: 1/1 ethyl acetate/hexane, $R_f=0.36$; 10% methanol/methylene chloride, $R_f=0.63$. IR (CHCl$_3$), NMR (CDCl$_3$) and mass spectra (M+ =430) are consistent with the assigned structure.

ANALYSIS: Calculated for $C_{24}H_{34}N_2O_5 \cdot HCL$ 61 73%C 7.55%H 6.00%N; Found: 62.10%C 7.53%H 5.95%N.

EXAMPLE 12

Preparation of 6-Deoxy-7-desacetyl-7-[[methylamino]carbonyl]-forskolin-1,9-dimethylformamide acetal To 1.51 g (3.70 mmol) of 6-deoxy-7-desacetylforskolin-1,9-dimethylformamide acetal (prepared as described in Example 4) in 150 ml of tetrahydrofuran was added 3.6 ml (3.70 mmol) of lithium bis(trimethylsilyl)amide. The solution was stirred at room temperature for 40 min. To the solution was added 0.42 ml (7.11 mmol) of methylisocyanate. The solution was stirred at room temperature for 3.5 hr, after which it was heated to 55° for 1 hr, and then at 40° C. for 0.5 hr. After being cooled to room temperature, the solution was poured into a mixture of ice/water/ethyl acetate, extracted with ethyl acetate, and the extracts were combined, washed with water (3X), saturated sodium chloride, dried over sodium sulfate, filtered and concentrated. The residue was dried at 110° for 6 hr to provide 0.658 g (1.41 mmol, 38%) of 6-deoxy-7-[[methylamino]carbonyl]forskolin-1,9-dimethylformamide acetal, mp 161°–162° C. The material appeared pure by thin layer chromatography on silica gel: 1:1 ethyl acetate/hexane, $R_f=0.31$; 10% methanol/methylene chloride, $R_f=0.56$; NMR(CDCl$_3$, D$_2$O), IR(CHCl$_3$) and mass spectra (MH+ =465) are consistent with the assigned structure.

ANALYSIS Calculated for $C_{25}H_{40}N_2O_6$: 64.63%C; 8.68%H 6.03%N; Found: 64.37%C; 8.61%H 5.92%N.

EXAMPLE 13

Preparation of 6-Deoxy-7-desacetyl-7-(pyridin-2-yl)forskolin hydrochloride

To 0.562 g (1.16 mmol) of 6-deoxy-7-desacetyl-7-(pyridin-2-yl)forskolin-1,9-dimethylformamide acetal (prepared as described in Example 10) was added 28 ml of a 1:3 mixture of water/methanol. The solution was stirred at 60°–70° C. under nitrogen for 18 hr and then cooled to room temperature and concentrated. The residue was purified by flash chromatography on silica gel, eluting with 20% ethyl acetate/hexane. The product-containing fractions were combined and concentrated. The residue was dried at 110° for 2 hr. The free base was dissolved in ether and ethereal hydrogen chloride was added. The resulting precipitated, white solid was collected by filtration and dried at 80° C. for 4 hr to provide 0.274 of (0.589 mmol, 50.7%) of 6-deoxy-7-desacetyl-7-(pyridin-2-yl)forskolin hydrochloride, mp 169°–170° (dec). The free base, regenerated with methylene chloride/sodium bicarbonate, appeared pure by thin layer chromatography on silica gel: 20% ethyl acetate/hexane, $R_f=0.14$; 10% methanol/methylene chloride, $R_f=0.75$. NMR(CDCl$_3$, D$_2$O), IR(CHCl$_3$), and mass spectra (MH+ =430) are consistent with the assigned structure.

ANALYSIS: Calculated for $C_{25}H_{35}NO_5 \cdot HCl$: 64.43%C 7.79%H 3.01%N; Found: 64.23%C 7.51%H 2.97%N.

EXAMPLE 14

Preparation of 6-Acetyl-7-desacetyl-7-imidazolothiocarbonyl-forskolin-1,9-dimethylformamide acetal A solution of 4.0 g (8.60 mmol) of 6-acetyl-7-desacetylforskolin-1,9-dimethylformamide acetal, 60 mg (0.405 mmol) of 4-pyrrolidinopyridine and 2.0 g (11.2 mmol) of 1,1-thiocarbonyldiimidazole was stirred at 100°–110° C. for 24 hr in a sealed tube. The solution was allowed to cool to room temperature and 1.0 g (5.6 mmol) of 1,1'-thiocarbonyldiimidazole was added. The solution was stirred at 100°–110° C. for 24 hr, allowed to cool to room temperature and flash chromatographed on silica gel, eluting with 20% ethyl acetate/hexanes followed by 40% ethyl acetate/hexanes. The product-containing fractions were combined and concentrated to provide 3.91 g (6.79 mmol, 79%) of a solid which, upon recrystallization from cyclohexane, provided colorless crystals of 6-acetyl-7-desacetyl-7-imidazolothiocarbonylforskolin 1,9-dimethylformamide acetal, mp 165°–168° C. The material appeared pure by thin layer chromatography on silica gel: 1/1 acetone/hexanes, $R_f=0.53$; 1/1 ethyl acetate/hexanes, $R_f=0.4$, IR(CHCl$_3$), NMR(CDCl$_3$) and mass spectra (MH+ =576) are consistent with the assigned structure.

ANALYSIS: Calculated for $C_{29}H_{41}N_3O_7S$: 60.50%C 7.18%H 7.30%N; Found: 60.74%C 7.19%H 7.28%N.

EXAMPLE 15

Preparation of 6-Deoxy-7-desacetyl-7-[[methylamino]carbonyl]forskolin

To 0.525 g (1.13 mmol) of 6-deoxy-7-desacetyl[[methylamino]carbonyl]forskolin-1,9-dimethylformamide acetal (prepared as described in Example 12) was added 27 ml of a 1:3 mixture of water/methanol. The solution was stirred at 60°–70° C. under nitrogen for 24 hr. The solution was cooled to room temperature and then concentrated. The residue was purified by flash chromatography on silica gel, eluting with 40% ethyl acetate/hexane. The product-containing fractions were combined and concentrated. The residue was dried at 110° C. for 5 hr to provide 0.408 g (0.996 mmol, 88%) of 6-deoxy-7-desacetyl-7-[[methylamino]carbonyl]forskolin, mp 159°–161° C. The material appeared pure by thin layer chromatography on silica gel: 40% ethyl acetate/hexane, $R_f=0.42$; 10% tetrahydrofuran/methylene chloride, $R_f=0.75$. NMR(CDCl$_3$, D$_2$O), IR(CHCl$_3$) and mass spectra (MH+ =410) are consistent with the assigned structure.

ANALYSIS: Calculated for $C_{22}H_{35}NO_6$: 64.52%C 8.61%H 3.42%N; Found: 64.00%C 8.86%H 3.33%N.

EXAMPLE 16

Preparation of
6-Deoxy-7-desacetyl-7-[[[(3-dimethylamino)-propyl]amino]carbonyl]forskolin-1,9-dimethylformamide acetal monohydrate To 2.02 g (4.95 mmol) of 6-deoxy-7-desacetylforskolin-1,9-dimethylformamide acetal (prepared as described in Example 4) in 40 ml of methylene chloride was added 0.961 g (5.94 mmol) of 1,1'-carbonyldiimidazole. The solution was stirred at room temperature under nitrogen for 72 hr and then 3.1 ml (24.6 mmol) of 3-dimethylaminopropylamine was added. The solution was stirred at room temperature under nitrogen, after which it was poured into a mixture of ice/water/ethyl acetate, and extracted with ethyl acetate. The extracts were washed with water, saturated sodium chloride, dried over sodium sulfate, filtered and concentrated. The oil was purified by flash chromatography on silica gel, eluting with 20% methanol/methylene chloride. The product-containing fractions were combined and concentrated. The impure fractions were again flash chromatographed, eluting with 80% acetone/hexane and the product-containing fractions were combined with those from the first chromatography and concentrated. The residue was dried at 110° C. for 5 hr to provide 1.59 g (2.97 mmol, 60%) of 6-deoxy-7-desacetyl-7-[[[(3-dimethylamino)propyl]amino]carbonyl]-forskolin 1,9-dimethylformamide acetal monohydrate, mp 55°–58° C. The material appeared pure by thin layer chromatography on silica gel: 20% methanol/methylene chloride, $R_f=0.20$; 80% acetone/hexane, $R_f=0.08$ NMR(CDCl$_3$, D$_2$O), IR(CHCl$_3$) and mass spectra (MH+ = 536) are consistent with the assigned structure.

ANALYSIS: Calculated for C$_{26}$H$_{49}$N$_3$O$_6$·H$_2$O: 62.70%C 9.28%H 7.59%N; Found: 63.18%C 9.10%H 7.63%N.

EXAMPLE 17

Preparation of
6-Acetyl-7-desacetoxy-7(H)forskolin-1,9-dimethylformamide acetal

To a stirred, refluxing solution of 200 mg (0.404 mmol) of 6-acetyl-7-desacetyl-7-imidazolothiocarbonyl-forskolin-1,9-dimethylformamide acetal (prepared as described in Example 14) in 10 ml of toluene was added a solution of 9 mg (0.55 mmol) of 2,2'-azobis(2-methylpropionitrile) in 2 ml of toluene followed by 0.8 ml (0.86 g, 2.97 mmol) of tri(n-butyl)tin hydride. The solution was stirred at reflux (115°–120°) for 1.5 hr and allowed to cool to room temperature. The reaction mixture was purified directly (without aqueous workup) by flash chromatography on silica gel, eluting with 10% ethyl acetate/hexanes followed by 15% ethyl acetate/hexanes. The pure, product-containing fractions were combined and concentrated to provide 0.106 g (0.236 mmol, 58.4%) of 6-acetyl-7-desacetoxyforskolin 1,9-dimethylformamide acetal, mp 118°–123° C. The material appeared pure by thin layer chromatography on silica gel: 20% ethyl acetate/hexanes, $R_f=0.19$; 30% acetone/hexanes, $R_f=0.51$. NMR(CDCl$_3$), IR(CHCl$_3$) and mass spectra (MH+ =450) are consistent with the assigned structure.

ANALYSIS: Calculated for C$_{25}$H$_{39}$NO$_6$: 66.79%C 8.74%H 3.12%N; Found: 66.73%C 8.79%H 3.06%N.

EXAMPLE 18

Preparation of
6-Deoxy-7-desacetyl-7-[[[(3-dimethylamino)propyl]amino]carbonyl]forskolin hydrochloride dihydrate To 0.429 g (.802 mmol) of.6-deoxy-7-desacetyl-7-[[[(3-dimethylamino)propyl]amino]carbonyl]forskolin-1,9-dimethylformamide acetal (prepared as described in Example 16) was added 22 ml of a 1:3 water/methanol mixture. The solution was heated to 60°–70° C. for 48 hr, after which it was concentrated in vacuo. The residue was purified by flash chromatography on silica gel, eluting with 20% methanol/ methylene chloride. The product-containing fractions were again flash chromatographed, eluting with 80% acetone/hexane and the product-containing fractions were combined and concentrated. The residue (free base) was dissolved in ether, and converted to the hydrochloride salt by addition of ethereal hydrogen chloride. The solvent was evaporated under high vacuum and the residue was dried and then triturated with ether. The ether was decanted and the residue was again dried under high vacuum and then dried at 80° C. for 2 hr to provide 0.230 g (0.445 mmol) of 6-deoxy-7-desacetyl-7-[[[(3-dimethylamino)propyl]amino]carbonyl]forskolin hydrochloride dihydrate, mp 178°–183° C. (dec.). The free base (regenerated with methylene chloride/sodium bicarbonate) appeared pure by thin layer chromatography on silica gel: 20% methanol/methylene chloride, $R_f=0.19$; 80% acetone/hexane, $R_f=0.09$. NMR(CDCl$_3$, D$_2$O), IR(CHCl$_3$) and mass spectra (MH+ =480) are consistent with the assigned structure.

ANALYSIS: Calculated for C$_{26}$H$_{44}$N$_2$O$_6$·HCl·2H$_2$O: 56.46%C 8.93%H 5.06%N; Found: 56..39%C 8.38%H 4.84%N.

EXAMPLE 19

Preparation of 6-Acetyl-7-desacetoxy-7(H)forskolin

A solution of 0.5 g (1.11 mmol) of 6-acetyl-7-desacetoxyforskolin-1,9-dimethylformamide acetal (prepared as described in Example 17) in 25 ml of methanol and 8 ml of water was stirred at 70°–80° C. for 16 hr. The solution was concentrated to a white solid which was purified by flash chromatography on silica gel, eluting with 15% ethyl acetate/hexanes followed by 20% ethyl acetate/hexanes. The pure product-containing fractions were combined and concentrated to provide 368 mg of a white solid which, upon recrystallization from ethyl acetate/hexanes, provided 305 mg (0.774 mmol, 69.7%) of colorless needles of 6-acetyl-7-desacetoxyforskolin, mp 186°–188° C. The material appeared pure by thin layer chromatography on silica gel: 30% ethyl acetate/hexanes, $R_f=0.27$; 30% acetone/hexanes, $R_f=0.39$. NMR(CDCl$_3$), IR(CHCl$_3$) and mass spectra (MH+ =394) were consistent with the assigned structure.

ANALYSIS Calculated for C$_{22}$H$_{32}$O$_6$: 66.98%C 8.69%H; Found: 67.06%C 8.61%H.

EXAMPLE 20

Preparation of
6-Deoxy-7-desacetyl-7-(2-chloropyrimidin-4-yl)forskolin-1,9-dimethylformamide acetal A mixture of 2.65 g (6.50 mmol) of 6-deoxy-7-desacetylforskolin 1,9-dimethylformamide acetal and 2.71 g (18.0 mmol) of 2,4-dichloropyrimidine was dissolved in 10 ml of toluene and twice azeotroped on a rotary evaporator. To the mixture was added 50 ml of dry tetrahydrofuran. The solution was cooled in an ice bath. To the solution at 0° C., was added portionwise 0.730 g (6.50 mmol) of potassium t-butoxide. The reaction mixture was stirred for 1.5 hr., after which it was poured into a mixture of ice, water and ether, extracted with ether, washed with water, saturated sodium chloride, dried over sodium sulfate, filtered and concentrated. To the residue was added 0.975 g (6.5 mmol) of 2,4-dichloropyrimidine. The mixture was dissolved in toluene and azeotroped twice and 50 ml of dry tetrahydrofuran was added. The resulting solution was cooled to 0° C., 0.751 g (6.70 mmol) of potassium t-butoxide was added portionwise, and the mixture was stirred at 0° C. under nitrogen for 1 hr. and then worked up as above. The residue was purified by flash chromatography, eluting with 10% acetone/hexane. The product containing fractions were combined and concentrated. The resulting oil was further purified by flash chromatography, eluting with 15% ethyl acetate/hexane. The product-containing fractions were combined and concentrated. The residue was dried at 110° C. for 2 hrs. to provide 0.790 g (0.152 mmol, 23%) of 6-deoxy-7-desacetyl-7-(2-chloropyrimidin-4-yl)forskolin-1,9-dimethylformamide acetal, mp 100°-101° C. The material appeared pure by thin layer chromatography on silica gel: 2% methanol/methylene chloride; $R_f=0.22$; ethyl acetate, $R_f=0.62$. NMR(CDCl$_3$, D$_2$O), IR(CHCl$_3$), and mass spectra(MH+ =520) are consistent with the assigned structure.

Analysis: Calculated for $C_{27}H_{38}ClN_3O_5$: 62.36%C 7.36%H 8.08%N; Found: 62.29%C 7.17%H 7.90%N.

EXAMPLE 21

Preparation of
6-Deoxy-7-desacetyl-7-(6-fluoropyridin-2-yl)forskolin-1,9-dimethylformamide acetal To 1.01 g (2.47 mmol) of 6-deoxy-7-desacetylforskolin-1,9-dimethylformamide acetal in 25 ml of tetrahydrofuran was added 0.276 g (2.46 mmol) of potassium t-butoxide. The suspension was stirred for several minutes, after which 0.268 ml (2.95 mmol) of 2,6-difluoropyridine was added and the solution stirred for 3 hr. The reaction mixture was then poured into a mixture of ice, water and methylene chloride, extracted with methylene chloride, washed with water, saturated sodium chloride, dried over sodium sulfate, filtered and concentrated. The oil was purified by flash chromatography eluting with 15% ethyl acetate/hexane. The product containing fractions were combined and concentrated. The residue was dried at 110° C. for 5 hours to provide 0.802 g (1.60 mmol, 65%) of 6-deoxy-7-desacetyl-7-(6-fluoropyridin-2-yl)forskolin-1,9-dimethylformamide acetal. The material appeared pure by thin layer chromatography on silica gel: 40% ethyl acetate/hexane, $R_f=0.70$; 30% acetone/hexane; $R_f=0.73$.

NMR (CDCl$_3$, D$_2$O), IR(CHCl$_3$) and mass spectra (MH+ =503) are consistent with the assigned structure.

Analysis: Calculated for $C_{28}H_{39}FN_2O_5$: 66.91%C 7.82%H 5.57%N; Found: 66.95%C 7.75%H 5.55%N.

EXAMPLE 22

Preparation of
6-Deoxy-7-desacetyl-7-(6-fluoro-pyridin-2-yl)forskolin

To 0.491 g (0.970 mmol) of 6-deoxy-7-(6-fluoropyridin-2-yl)forskolin-1,9-dimethylformamide acetal was added 24 ml of a 1:3 mixture of water/methanol. The reaction mixture was heated to 60°-70° C. for 6 hr, after which it was concentrated in vacuo. The residue was purified by flash chromatography eluting with 30% acetone/hexane. The product containing fractions were combined and concentrated. The residue was recrystallized from cyclohexane/ethyl acetate. The resulting crystals were dried at 110° C. for 2 hr to yield 0.304 g (0.680 mmol, 70%) of 6-deoxy-7-desacetyl-7(6-fluoropyridin-2-yl)forskolin. The material appeared pure by thin layer chromatography: 30% acetone/hexane, $R_f=0.46$; 50% ethyl acetate/hexane, $R_f=0.41$. NMR (CDCl$_3$, D$_2$O) ,I R (CHCl$_3$), and mass spectra (MH+ =448) are consistent with the assigned structure.

Analysis: Calculated for $C_{25}H_{34}FNO_5$: 67.09%C 7.66%H 3.13%N; Found: 66.99%C 7.52%H 3.12N.

EXAMPLE 23

Preparation of
6-Deoxy-7-desacetyl-7-[6-(morpholin-4-yl)pyridin-2-yl]forskolin

To 0.809 g (1.81 mmol) of 6-deoxy-7-desacetyl-7-(2-fluoropyridin-2-yl)forskolin in 4 ml of ethanol was added 0.24 ml (2.75 mmol) of morpholine and 2 drops of ethereal hydrogen chloride. The mixture was heated to 110° C. in a sealed tube. After several hours an additional 0.24 ml (2.75 mmol) of morpholine was added. The solution was stirred for 24 hr at 110° C., after which was added another 0.05 ml (0.057 mmol) of morpholine. The solution was stirred for 24 hr at 110° C., then cooled to room temperature and poured into a mixture of ether and water, extracted with ether, washed with water, washed with saturated sodium chloride, dried over sodium sulfate, filtered and concentrated. The residue was concentrated in vacuo and recrystallized from ethyl acetate/cyclohexane. The residue was further purified by flash chromatography, eluting with 5% acetone/hexane and the product-containing fractions were combined and concentrated. The residue was dried at 110° C. for 3 hrs. to provide 0.20 g (0.39 mmol) of 6-deoxy-7-desacetyl-7-[6-(morpholin-4-yl)pyridin-2-yl]forskolin, m.p. 213°-215° C. The material appeared pure by this layer chromatography on silica gel: 30% acetone/hexane, $R_f=0.29$; 50% ethyl acetate/hexane, $R_f=0.40$. NMR(CDCl$_3$, D$_2$O), mass spectra(MH+ =514) and IR(CHCl$_3$) are consistent with the assigned structure Analysis: Calculated for $C_{29}H_{42}N_2O$: 67.68%C 8.23%H 5.44%N; Found: 67.63%C 7.90%H 5.37%N.

REACTION SCHEME A
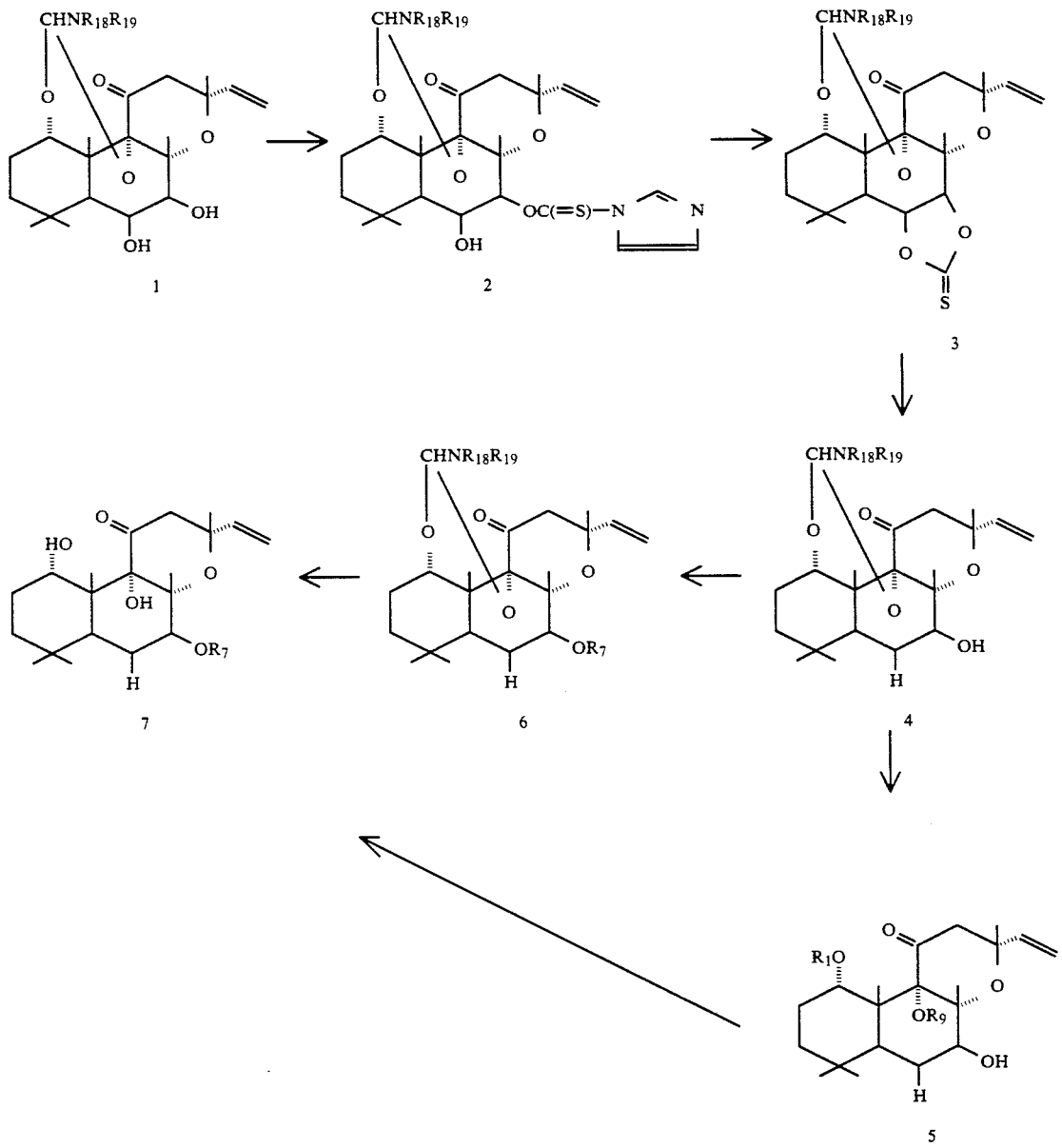
REACTION SCHEME B
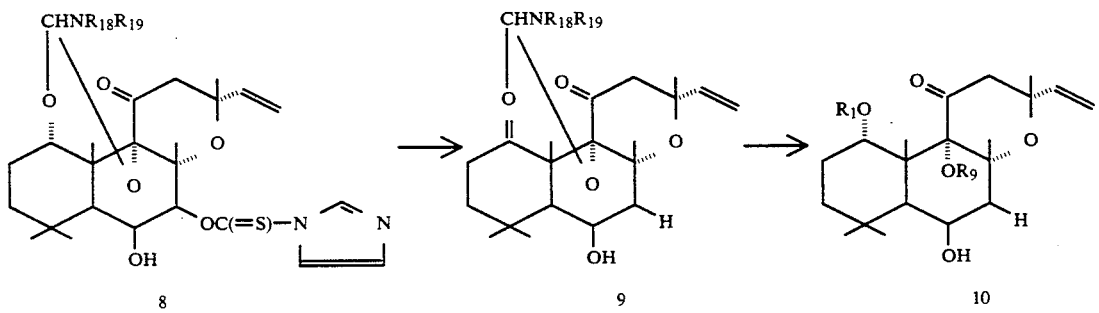

-continued
REACTION SCHEME B

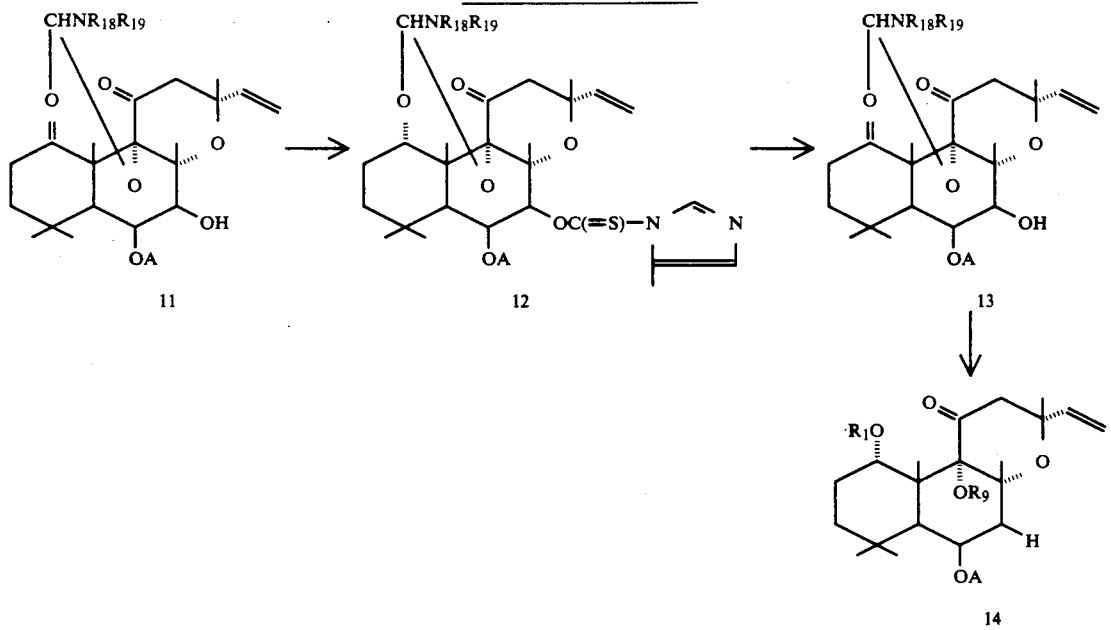

We claim:

1. A method for treating hypertension in mammals comprising administering to a mammal requiring treatment for hypertension a hypertension treating effective amount of a composition comprising an inert adjuvant and a pharmaceutically effective amount of a compound of formula

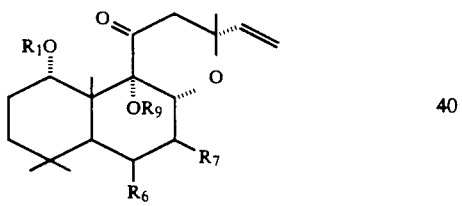

wherein
$R_1$ is hydrogen, loweralkyl arylloweralkyl, a group of formula $R_2R_3R_4Si$, a group of formula $R_5CO$, a group of formula $R_8R_{10}N(CHR_{11})_nCO$ wherein n is 0 or 1, or Ar';
$R_6$ is hydrogen, hydroxyl, a group of formula $OR_{12}$, a group of formula $OCOR_{13}$, a group of formula $OCONR_{14}R_{15}$, or a group of formula OAr;
$R_7$ is defined as $R_6$, or is a group of formula $OCOR_{16}$, a group of formula $OCONR_{17}Z$, a group of formula OAr', a group of formula OCOAr', a group of formula $OCONR_{17}Ar'$, or a group of formula

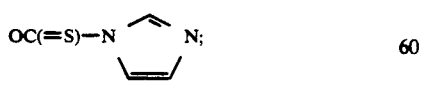

$R_6$ and $R_7$ taken together form a group of formula O—C(=S)—O;
$R_9$ is hydrogen;
or $R_1$ and $R_9$ may be taken together to form a group of formula CO, or a group of formula SO or a group of formula $CHNR_{18}R_{19}$;

$R_2$, $R_3$, and $R_4$ are the same or not all the same and each is loweralkyl;
$R_5$ is hydrogen or loweralkyl;
$R_8$, $R_{10}$ and $R_{11}$ are the same or not all the same and each is hydrogen, loweralkyl or arylloweralkyl;
$R_8$ and $R_{10}$ taken together with the nitrogen atom to which they are attached form a group of formula

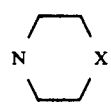

wherein
X is CO, O, S, a group of formula $CHR_{20}$ or a group of formula $NR_{21}$;
$R_{12}$ is loweralkyl or alkylaminoloweralkyl;
$R_{13}$ is hydrogen, straight or branched chain alkyl containing from 1 to 20 carbon atoms, —CH(OH)CH$_2$OH,

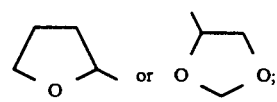

$R_{14}$ is hydrogen, loweralkyl, hydroxyloweralkyl, loweralkoxyloweralkyl, or a group of formula HOCH$_2$CH(OH)CH$_2$;
$R_{15}$ is hydrogen, hydroxyl, loweralkoxy, loweralkyl, hydroxyloweralkyl, loweralkoxyloweralkyl, loweralkanoyl, loweralkanoylloweralkyl, a group of formula

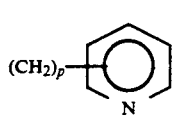

wherein p is 1 or 2, a group of formula

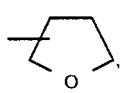

a group of formula HOCH$_2$(OH)CH$_2$, a group of formula (CH$_2$)$_q$NR$_{22}$R$_{23}$ wherein q is an integer equalling 0 or from 2 to 6, a group of formula OR$_{24}$ or a group of formula OCOR$_{25}$;

R$_{16}$ is hydroxyloweralkyl,

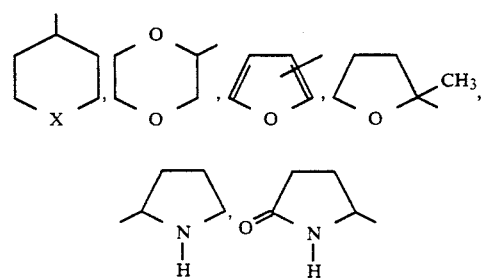

wherein X is as defined above, a group of formula R$_{26}$OCR$_{27}$R$_{28}$(CH$_2$)$_r$ wherein r is 0, 1, 2 or 3, a group of formula R$_{29}$R$_{30}$N(CH$_2$)$_s$(CHR$_{31}$)(CH$_2$)$_{s'}$, wherein s and s' are the same or different and each is 0, 1 or 2, or a group of formula (CH$_2$)$_f$CO$_2$H, wherein f is an integer from 0 through 5;

R$_{17}$ is hydrogen or loweralkyl;

R$_{18}$ and R$_{19}$ are the same or different and each is loweralkyl;

R$_{18}$ and R$_{19}$ taken together with the nitrogen atom to which they are attached form a group of formula

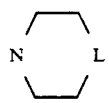

wherein L is O, S or CHR$_{20}$;

R$_{20}$ is hydrogen or loweralkyl;

R$_{21}$ is hydrogen or loweralkyl;

R$_{22}$ and R$_{23}$ are the same or different and each is loweralkyl;

R$_{22}$ and R$_{23}$ taken together with the nitrogen atom to which they are attached form a group of formula

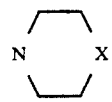

wherein X is defined as above;

R$_{24}$ is hydrogen, loweralkyl a group of formula (CH$_2$)$_q$NR$_{22}$R$_{23}$ wherein R$_{22}$, R$_{23}$ and q are as defined above;

R$_{25}$ is hydrogen, loweralkyl, lowercycloalkyl of 3 to 6 carbon atoms, haloloweralkenyl, loweralkanoylloweralkyl, loweralkoxyloweralkyl, loweralkoxycarbonylloweralkyl, loweralkylamino, lowerdialkylamino, a group of formula

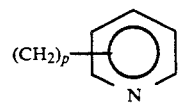

wherein p is defined as above, a group of formula

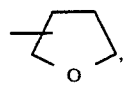

a group of the formula (CH$_2$)$_q$NR$_{22}$R$_{23}$ wherein R$_{22}$, R$_{23}$ and q are as defined above, a group of formula

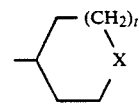

wherein x is as defined above and t is 0 or 1, or a group of formula (CH$_2$)$_u$N(R$_{33}$)COR$_{34}$ wherein u is 1, 2 or 3;

R$_{26}$, R$_{27}$ and R$_{28}$ are the same or not all the same and each is hydrogen or loweralkyl;

R$_{29}$ is hydrogen, loweralkyl, or a group of formula R$_{35}$CO;

R$_{30}$ is hydrogen or loweralkyl;

R$_{29}$ and R$_{30}$ taken together with the nitrogen atom to which they are attached form a group of formula

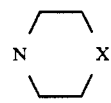

wherein X is defined above;

R$_{31}$ is hydrogen, loweralkyl, arylloweralkyl or hydroxyl;

R$_{33}$, R$_{34}$ and R$_{35}$ are the same or not all the same and each is hydrogen or loweralkyl;

Ar is phenyl, naphthyl, pyridinyl, pyridazinyl or pyrimidinyl, each of which is unsubstituted or mono- or poly-substituted by loweralkyl, halogen or nitro;

Ar' is phenyl, naphthyl, pyridinyl, pyridazinyl, pyrimidinyl, furanyl, oxazolyl, purinyl or thiazolyl, each of which is unsubstituted or mono- or poly-substituted by loweralkyl, halogen, nitro, or a group of formula NR$_{34'}$R$_{35'}$, or phenyl, naphthyl, pyridinyl or pyrimidinyl, each of which is mono- or poly-substituted by a group of formula NR$_{34'}$R$_{35'}$;

R$_{34'}$ and R$_{35'}$ are the same or different and each is hydrogen, loweralkyl or alkylaminoloweralkyl;

R$_{34'}$ and R$_{35'}$ taken together with the nitrogen atom to which they are attached form a group of formula

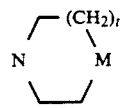

wherein M is NR$_{47}$, O or CH$_2$ and y is 0, 1 or 2;

Z is a group of formula $(CH_2)_vNR_{37}R_{38}$ wherein v is 0 or an integer from 2 to 5, a group of formula $N=CR_{39}R_{40}$ or a group of formula $(CH_2)_gCO_2H$ wherein g is an integer from 0 to 5;

Z and $R_{17}$ and the nitrogen to which they are attached form a group

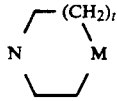

wherein M is $NR_{47}$, O or $CH_2$ and y is 0, 1 or 2;

$R_{37}$ and $R_{38}$ are the same or different and each is hydrogen, loweralkyl or a group of formula $COR_{41}$;

$R_{37}$ and $R_{38}$ taken together with a nitrogen atom to which they are attached form a group of formula

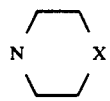

wherein X is defined as above;

$R_{39}$ is loweralkyl;

$R_{40}$ is loweralkyl, loweralkenyl, a group of formula

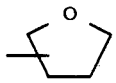

or a group of formula

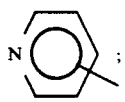

$R_{39}$ and $R_{40}$ taken together with the carbon atom to which they are attached form a group of formula

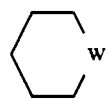

wherein W is O, a group of the formula $NR_{42}$, or a group of formula $CHR_{43}$;

$R_{41}$ s loweralkyl or a group of formula $(CH_2)_xNR_{44}R_{45}$ wherein x is an integer from 0 to 5;

$R_{42}$ is loweralkyl;

$R_{43}$ is hydrogen, loweralkyl or a group of formula $OR_{46}$;

$R_{44}$ and $R_{45}$ are the same or different and each is loweralkyl;

$R_{46}$ is loweralkyl;

$R_{47}$ is hydrogen, loweralkyl or (C=O) loweralkyl; and the optical and geometric isomers thereof, or a pharmaceutically acceptable salt thereof, provided:

(a) if $R_6$ is hydrogen, then $R_7$ is not hydrogen;

(b) if $R_7$ is hydrogen, hen $R_6$ is not hydrogen; and (c) if neither $R_6$ nor $R_7$ is hydrogen, then $R_6$ is OH, $R_{13}(C(=O)O$, a group of formula $OR_{12}$, a group of formula $OCONR_{14}R_{15}$ or a group of formula OAr, and $R_7$ is

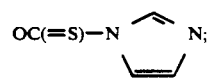

or, $R_6$ and $R_7$ taken together form a group of formula O—C(=S)—O.

2. A method for treating memory deficit in mammals comprising administering to a mammal requiring treatment for memory deficit a memory deficit treating effective amount of a composition comprising an inert adjuvant and a pharmaceutically effective amount of a compound of formula

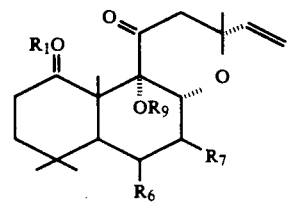

wherein $R_1$ is hydrogen, loweralkyl arylloweralkyl, a group of formula $R_2R_3R_4Si$, a group of formula $R_5CO$, a group of formula $R_8R_{10}N(CHR_{11})_nCO$ wherein n is 0 or 1, or Ar';

$R_6$ is hydrogen, hydroxyl, a group of formula $OR_{12}$, a group of formula $OCOR_{13}$, a group of formula $OCONR_{14}R_{15}$, or a group of formula OAr;

$R_7$ is defined as $R_6$, or is a group of formula $OCOR_{16}$, a group of formula $OCONR_{17}Z$, a group of formula OAr', a group of formula OCOAr', a group of formula $OCONR_{17}Ar'$, or a group of formula

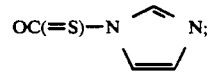

$R_6$ and $R_7$ taken together form a group of formula O—C(=S)—O;

$R_9$ is hydrogen;

or $R_1$ and $R_9$ may be taken together to form a group of formula CO, or a group of formula SO or a group of formula $CHNR_{18}R_{19}$;

$R_2$, $R_3$, and $R_4$ are the same or not all the same and each is loweralkyl;

$R_5$ is hydrogen or loweralkyl;

$R_8$, $R_{10}$ and $R_{11}$ are the same or not all the same and each hydrogen, loweralkyl or arylloweralkyl;

$R_8$ and $R_{10}$ taken together with the nitrogen atom to which they are attached form a group of formula

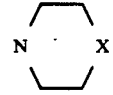

wherein

X is CO, O, S, a group of formula $CHR_{20}$ or a group of formula $NR_{21}$;

$R_{12}$ is loweralkyl or alkylaminoloweralkyl;

$R_{13}$ is hydrogen, straight or branched chain alkyl containing from 1 to 20 carbon atoms, —CH(OH)CH$_2$OH,

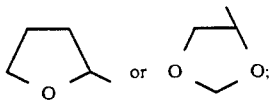

$R_{14}$ is hydrogen, loweralkyl, hydroxyloweralkyl, loweralkoxyloweralkyl, or a group of formula HOCH$_2$CH(OH)CH$_2$;

$R_{15}$ is hydrogen, hydroxyl, loweralkoxy, loweralkyl, hydroxyloweralkyl, loweralkoxyloweralkyl, loweralkanoyl, loweralkanoylloweralkyl, a group of formula

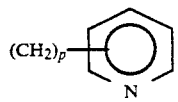

wherein p is 1 or 2, a group of formula

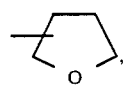

a group of formula HOCH$_2$(OH)CH$_2$, a group of formula (CH$_2$)$_q$NR$_{22}$R$_{23}$ wherein q is an integer equalling 0 or from 2 to 6, a group of formula OR$_{24}$ or a group of formula OCOR$_{25}$;

$R_{16}$ is hydroxyloweralkyl,

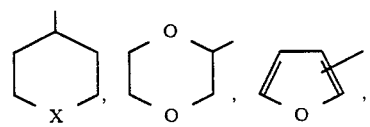

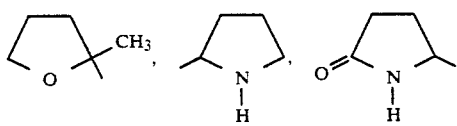

wherein X is as defined above, a group of formula R$_{26}$OCR$_{27}$R$_{28}$(CH$_2$)$_r$ wherein r is 0, 1, 2 or 3, a group of formula R$_{29}$R$_{30}$N(CH$_2$)$_s$(CHR$_{31}$)(CH$_2$)$_{s'}$, wherein s and s' are the same or different and each is 0, 1 or 2, or a group of formula (CH$_2$)$_f$CO$_2$H, wherein f is an integer from 0 through 5;

$R_{17}$ is hydrogen or loweralkyl;

$R_{18}$ and $R_{19}$ are the same or different and each is loweralkyl;

$R_{18}$ and $R_{19}$ taken together with the nitrogen atom to which they are attached form a group of formula

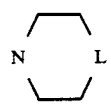

wherein L is O, S or CHR$_{20}$;
$R_{20}$ is hydrogen or loweralkyl;

$R_{21}$ is hydrogen or loweralkyl;

$R_{22}$ and $R_{23}$ are the same or different and each is loweralkyl;

$R_{22}$ and $R_{23}$ taken together with the nitrogen atom to which they are attached form a group of formula

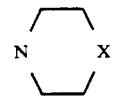

wherein X is defined as above;

$R_{24}$ is hydrogen, loweralkyl, a group of formula (CH$_2$)$_q$NR$_{22}$R$_{23}$ wherein R$_{22}$, R$_{23}$ and q are as defined above;

$R_{25}$ is hydrogen, loweralkyl, lowercycloalkyl of 3 to 6 carbon atoms, haloloweralkenyl, loweralkanoylloweralkyl, loweralkoxyloweralkyl, loweralkoxycarbonylloweralkyl, loweralkylamino, lowerdialkylamino, a group of formula

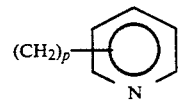

wherein p is defined as above, a group of formula

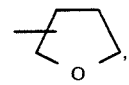

a group of formula (CH$_2$)$_q$NR$_{22}$R$_{23}$ wherein R$_{22}$, R$_{23}$ and q are as defined above, a group of formula

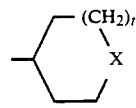

wherein X is as defined above and t is 0 or 1, or a group of formula (CH$_2$)$_u$N(R$_{33}$)COR$_{34}$ wherein u is 1, 2 or 3;

$R_{26}$, $R_{27}$ and $R_{28}$ are the same or not all the same and each is hydrogen or loweralkyl;

$R_{29}$ is hydrogen, loweralkyl or a group of formula R$_{35}$CO;

$R_{30}$ is hydrogen or loweralkyl;

$R_{29}$ and $R_{30}$ taken together with the nitrogen atom to which they are attached form a group of formula

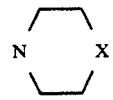

wherein X is defined above;

$R_{31}$ is hydrogen, loweralkyl, arylloweralkyl or hydroxyl;

$R_{33}$, $R_{34}$ and $R_{35}$ are the same or not all the same and each is hydrogen or loweralkyl;

Ar is phenyl, naphthyl, pyridinyl, pyridazinyl or pyrimidinyl, each of which is unsubstituted or mono- or poly-substituted by loweralkyl, halogen or nitro;

Ar' is phenyl, naphthyl, pyridinyl, pyridazinyl, pyrimidinyl, furanyl, oxazolyl, purinyl or thiazolyl, each of which is unsubstituted or mono- or poly-substituted by loweralkyl, halogen, nitro, or a group of formula NR$_{34'}$R$_{35'}$, or phenyl, naphthyl, pyridinyl or pyrimidinyl, each of which is mono- or poly-substituted by a group of formula NR$_{34'}$R$_{35'}$;

R$_{34'}$ and R$_{35'}$ are the same or different and each is hydrogen, loweralkyl or alkylaminoloweralkyl;

R$_{34'}$ and R$_{35'}$ taken together with the nitrogen atom to which they are attached form a group of formula

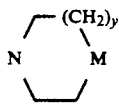

wherein M is NR$_{47}$, O or CH$_2$ and y is 0, 1 or 2;

Z is a group of formula (CH$_2$)$_v$NR$_{37}$R$_{38}$ wherein v is 0 or an integer from 2 to 5, a group of formula N=CR$_{39}$R$_{40}$ or a group of formula (CH$_2$O$_g$CO$_2$H wherein g is an integer from 0 to 5;

Z and R$_{17}$ and the nitrogen to which they are attached form a group

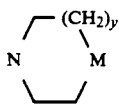

wherein M is NR$_{47}$, O or CH$_2$ and y is 0, 1 or 2;

R$_{37}$ and R$_{38}$ are the same or different and each is hydrogen, loweralkyl or a group of formula COR$_{41}$;

R$_{37}$ and R$_{38}$ taken together with the nitrogen atom to which they are attached form a group of formula

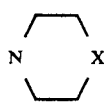

wherein X is defined as above;

R$_{39}$ is loweralkyl;

R$_{40}$ is loweralkyl, loweralkenyl, a group of formula

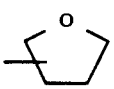

or a group of formula

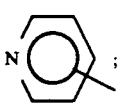

R$_{39}$ and R$_{40}$ taken together with the carbon atom to which they are attached form a group of formula

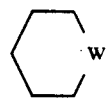

wherein W is O, a group of the formula NR$_{42}$, or a group of formula CHR$_{43}$;

R$_{41}$ is loweralkyl or a group of formula (CH$_2$)$_x$NR$_{44}$R$_{45}$ wherein x is an integer from 0 to 5;

R$_{42}$ is loweralkyl;

R$_{43}$ is hydrogen, loweralkyl or a group of formula OR$_{46}$;

R$_{44}$ and R$_{45}$ are the same or different and each is loweralkyl;

R$_{46}$ is loweralkyl;

R$_{47}$ is hydrogen, loweralkyl or (C=O)loweralkyl; and the optical and geometric isomers thereof, or a pharmaceutically acceptable salt thereof, provided:

(a) if R$_6$ is hydrogen, then R$_7$ is not hydrogen;

(b) if R$_7$ is hydrogen, then R$_6$ is not hydrogen; and (c) if neither R$_6$ nor R$_7$ is hydrogen, then R$_6$ is OH, R$_{13}$C(=O)O, a group of formula OR$_{12}$, a group of formula OCONR$_{14}$R$_{15}$ or a group of formula OAr, and R$_7$ is

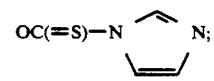

or, R$_6$ and R$_7$ taken together form a group of formula O—C(=S)—O.

3. A method for treating senile dementia in mammals comprising administering to a mammal requiring treatment for senile dementia a senile dementia treating effective amount of a composition comprising an inert adjuvant and a pharmaceutically effective amount of a compound of formula

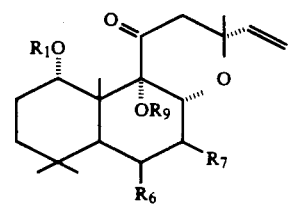

wherein

R$_1$ is hydrogen, loweralkyl arylloweralkyl, a group of formula R$_2$R$_3$R$_4$Si, a group of formula R$_5$CO, a group of formula R$_8$R$_{10}$N(CHR$_{11}$)$_n$CO wherein n is 0 or 1, or Ar';

R$_6$ is hydrogen, hydroxyl, a group of formula OR$_{12}$, a group of formula OCOR$_{13}$, a group of formula OCONR$_{14}$R$_{15}$, or a group of formula OAr;

R$_7$ is defined as R$_6$, or is a group of formula OCOR$_{16}$, a group of formula OCONR$_{17}$Z, a group of formula OAr', a group of formula OCOAr', a group of formula OCONR$_{17}$Ar', or a group of formula

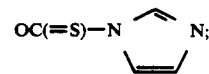

R6 and R7 taken together form a group of formula O—C(=S)—O;

R9 is hydrogen;

or R1 and R9 may be taken together to form a group of formula CO, or a group of formula SO or a group of formula CHNR18R19;

R2, R3, and R4 are the same or not all the same and each is loweralkyl;

R5 is hydrogen or loweralkyl;

R8, R10 and R11 are the same or not all the same and each is hydrogen, loweralkyl or arylloweralkyl;

R8 and R10 taken together with the nitrogen atom to which they are attached form a group of formula

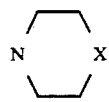

wherein

X is CO, O, S, a group of formula CHR20 or a group of formula NR21;

R12 is loweralkyl or alkylaminoloweralkyl;

R13 is hydrogen, straight or branched chain alkyl containing from 1 to 20 carbon atoms, —CH(OH)CH2OH,

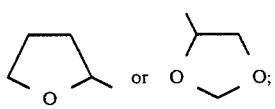

R14 is hydrogen, loweralkyl, hydroxyloweralkyl, loweralkoxyloweralkyl, or a group of formula HOCH2CH(OH)CH2;

R15 is hydrogen, hydroxyl, loweralkoxy, loweralkyl, hydroxyloweralkyl, loweralkoxyloweralkyl, loweralkanoyl, loweralkanoylloweralkyl, a group of formula

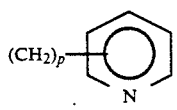

wherein p is 1 or 2, a group of formula

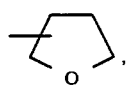

a group of formula HOCH2(OH)CH2, a group of formula (CH2)qNR22R23 wherein q is an integer equalling 0 or from 2 to 6, a group of formula OR24 or a group of formula OCOR25;

R16 is hydroxyloweralkyl,

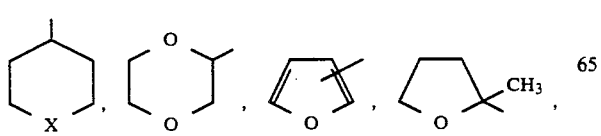

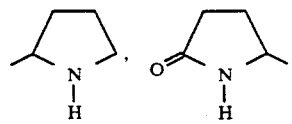

wherein X is as defined above, a group of formula R26OCR27R28(CH2)r wherein r is 0, 1, 2 or 3, a group of formula R29R30N(CH2)s(CHR31)(CH2)s', wherein s and s' are the same or different and each is 0, 1 or 2, or a group of formula (CH2)fCO2H, wherein f is an integer from 0 through 5;

R17 is hydrogen or loweralkyl;

R18 and R19 are the same or different and each is loweralkyl;

R18 and R19 taken together with the nitrogen atom to which they are attached form a group of formula

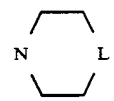

wherein L is O, S or CHR20;

R20 is hydrogen or loweralkyl;

R21 is hydrogen or loweralkyl;

R22 and R23 are the same or different and each is loweralkyl;

R22 and R23 taken together with the nitrogen atom to which they are attached form a group of formula

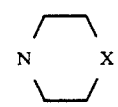

wherein X is defined as above;

R24 is hydrogen, loweralkyl a group of formula (CH2)qNR22R23 wherein R22, R23 and q are as defined above;

R25 is hydrogen, loweralkyl, lowercycloalkyl of 3 to 6 carbon atoms, haloloweralkenyl, loweralkanoylloweralkyl, loweralkoxyloweralkyl, loweralkoxycarbonylloweralkyl, loweralkylamino, lowerdialkylamino, a group of formula

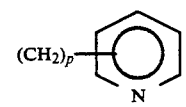

wherein p is defined as above, a group of formula

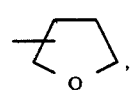

a group of the formula (CH2)qNR22R23 wherein R22, R23 and q are as defined above, a group of formula

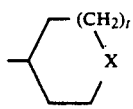

wherein x is as defined above and t is 0 or 1, or a group of formula $(CH_2)_uN(R_{33})COR_{34}$ wherein u is 1, 2 or 3;

$R_{26}$, $R_{27}$ and $R_{28}$ are the same or not all the same and each is hydrogen or loweralkyl;

$R_{29}$ is hydrogen, loweralkyl, or a group of formula $R_{35}CO$;

$R_{30}$ is hydrogen or loweralkyl;

$R_{29}$ and $R_{30}$ taken together with the nitrogen atom to which they are attached form a group of formula

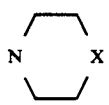

wherein X is defined above;

$R_{31}$ is hydrogen, loweralkyl, arylloweralkyl or hydroxyl;

$R_{33}$, $R_{34}$ and $R_{35}$ are the same or not all the same and each is hydrogen or loweralkyl;

Ar is phenyl, naphthyl, pyridinyl, pyridazinyl or pyrimidinyl, each of which is unsubstituted or mono- or poly-substituted by loweralkyl, halogen or nitro;

Ar' is phenyl, naphthyl, pyridinyl, pyridazinyl, pyrimidinyl, furanyl, oxazolyl, purinyl or thiazolyl, each of which is unsubstituted or mono- or poly-substituted by loweralkyl, halogen, nitro, or a group of formula $NR_{34'}R_{35'}$, or phenyl, naphthyl, pyridinyl or pyrimidinyl, each of which is mono- or poly-substituted by a group of formula $NR_{34'}R_{35'}$;

$R_{34'}$ and $R_{35'}$ are the same or different and each is hydrogen, loweralkyl or alkylaminoloweralkyl;

$R_{34'}$ and $R_{35'}$ taken together with the nitrogen atom to which they are attached form a group of formula

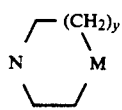

wherein M is $NR_{47}$, O or $CH_2$ and y is 0, 1 or 2;

Z is a group of formula $(CH_2)_vNR_{37}R_{38}$ wherein v is 0 or an integer from 2 to 5, a group of formula $N=CR_{39}R_{40}$ or a group of formula $(CH_2)_gCO_2H$ wherein g is an integer from 0 to 5;

Z and $R_{17}$ and the nitrogen to which they are attached form a group

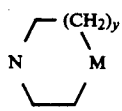

wherein M is $NR_{47}$, O or $CH_2$ and y is 0, 1 or 2;

$R_{37}$ and $R_{38}$ are the same or different and each is hydrogen, loweralkyl or a group of formula $COR_{41}$;

$R_{37}$ and $R_{38}$ taken together with a nitrogen atom to which they are attached form a group of formula

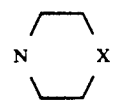

wherein X is defined as above;

$R_{39}$ is loweralkyl;

$R_{40}$ is loweralkyl, loweralkenyl, a group of formula

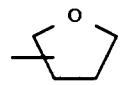

or a group of formula

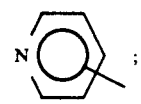

$R_{39}$ and $R_{40}$ taken together with the carbon atom to which they are attached form a group of formula

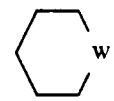

wherein W is O, a group of the formula $NR_{42}$, or a group of formula $CHR_{43}$;

$R_{41}$ s loweralkyl or a group of formula $(CH_2)_xNR_{44}R_{45}$ wherein x is an integer from 0 to 5;

$R_{42}$ is loweralkyl;

$R_{43}$ is hydrogen, loweralkyl or a group of formula $OR_{46}$;

$R_{44}$ and $R_{45}$ are the same or different and each is loweralkyl;

$R_{46}$ is loweralkyl;

$R_{47}$ is hydrogen, loweralkyl or (C=O) loweralkyl; and the optical and geometric isomers thereof, or a pharmaceutically acceptable salt thereof, provided:

(a) if $R_6$ is hydrogen, then $R_7$ is not hydrogen;

(b) if $R_7$ is hydrogen, hen $R_6$ is not hydrogen; and (c) if neither $R_6$ nor $R_7$ is hydrogen, then $R_6$ is OH, $R_{13}(C(=O)O$, a group of formula $OR_{12}$, a group of formula $OCONR_{14}R_{15}$ or a group of formula OAr, and $R_7$ is

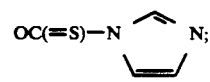

or, $R_6$ and $R_7$ taken together form a group of formula $O-C(=S)-O$.

4. A method for treating bronchial asthma in mammals comprising administering to a mammal requiring treatment for bronchial asthma a bronchial asthma treating effective amount of a composition comprising an inert adjuvant and a pharmaceutically effective amount of a compound of formula

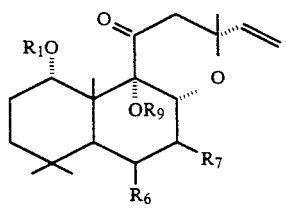

wherein
- R₁ is hydrogen, loweralkyl arylloweralkyl, a group of formula R₂R₃R₄Si, a group of formula R₅CO, a group of formula R₈R₁₀N(CHR₁₁)$_n$CO wherein n is 0 or 1, or Ar';
- R₆ is hydrogen, hydroxyl, a group of formula OR₁₂, a group of formula OCOR₁₃, a group of formula OCONR₁₄R₁₅, or a group of formula OAr;
- R₇ is defined as R₆, or is a group of formula OCOR₁₆, a group of formula OCONR₁₇Z, a group of formula OAr', a group of formula OCOAr', a group of formula OCONR₁₇Ar', or a group of formula

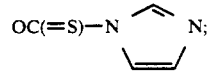

- R₆ and R₇ taken together form a group of formula O—C(=S)—O;
- R₉ is hydrogen;
- or R₁ and R₉ may be taken together to form a group of formula CO, or a group of formula SO or a group of formula CHNR₁₈R₁₉;
- R₂, R₃, and R₄ are the same or not all the same and each is loweralkyl;
- R₅ is hydrogen or loweralkyl;
- R₈, R₁₀ and R₁₁ are the same or not all the same and each is hydrogen, loweralkyl or arylloweralkyl;
- R₈ and R₁₀ taken together with the nitrogen atom to which they are attached form a group of formula

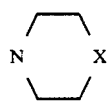

wherein
X is CO, O, S, a group of formula CHR₂₀ or a group of formula NR₂₁;
- R₁₂ is loweralkyl or alkylaminoloweralkyl;
- R₁₃ is hydrogen, straight or branched chain alkyl containing from 1 to 20 carbon atoms, —CH(OH)CH₂OH,

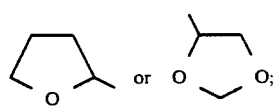

- R₁₄ is hydrogen, loweralkyl, hydroxyloweralkyl, loweralkoxyloweralkyl, or a group of formula HOCH₂CH(OH)CH₂;
- R₁₅ is hydrogen, hydroxyl, loweralkoxy, loweralkyl, hydroxyloweralkyl, loweralkoxyloweralkyl, loweralkanoyl, loweralkanoylloweralkyl, a group of formula

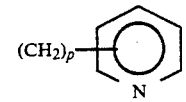

wherein p is 1 or 2, a group of formula

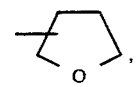

a group of formula HOCH₂(OH)CH₂, a group of formula (CH₂)$_q$NR₂₂R₂₃ wherein q is an integer equalling 0 or from 2 to 6, a group of formula OR₂₄ or a group of formula OCOR₂₅;

R₁₆ is hydroxyloweralkyl,

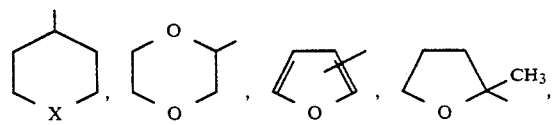

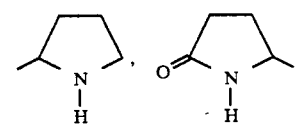

wherein X is as defined above, a group of formula R₂₆OCR₂₇R₂₈(CH₂)$_r$ wherein r is 0, 1, 2 or 3, a group of formula R₂₉R₃₀N(CH₂)$_s$(CHR₃₁)(CH₂)$_{s'}$, wherein s and s' are the same or different and each is 0, 1 or 2, or a group of formula (CH₂)$_f$CO₂H, wherein f is an integer from 0 through 5;

- R₁₇ is hydrogen or loweralkyl;
- R₁₈ and R₁₉ are the same or different and each is loweralkyl;
- R₁₈ and R₁₉ taken together with the nitrogen atom to which they are attached form a group of formula

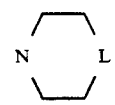

wherein L is O, S or CHR₂₀;
- R₂₀ is hydrogen or loweralkyl;
- R₂₁ is hydrogen or loweralkyl;
- R₂₂ and R₂₃ are the same or different and each is loweralkyl;
- R₂₂ and R₂₃ taken together with the nitrogen atom to which they are attached form a group of formula

wherein X is defined as above;
- R₂₄ is hydrogen, loweralkyl a group of formula (CH₂)$_q$NR₂₂R₂₃ wherein R₂₂, R₂₃ and q are as defined above;

$R_{25}$ is hydrogen, loweralkyl, lowercycloalkyl of 3 to 6 carbon atoms, haloloweralkenyl, loweralkanoyl-loweralkyl, loweralkoxyloweralkyl, loweralkoxycarbonylloweralkyl, loweralkylamino, lowerdialkylamino, a group of formula

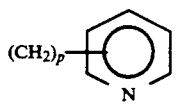

wherein p is defined as above, a group of formula

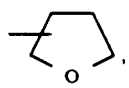

a group of the formula $(CH_2)_qNR_{22}R_{23}$ wherein $R_{22}$, $R_{23}$ and q are as defined above, a group of formula

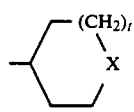

wherein x is as defined above and t is 0 or 1, or a group of formula $(CH_2)_uN(R_{33})COR_{34}$ wherein u is 1, 2 or 3;

$R_{26}$, $R_{27}$ and $R_{28}$ are the same or not all the same and each is hydrogen or loweralkyl;

$R_{29}$ is hydrogen, loweralkyl, or a group of formula $R_{35}CO$;

$R_{30}$ is hydrogen or loweralkyl;

$R_{29}$ and $R_{30}$ taken together with the nitrogen atom to which they are attached form a group of formula

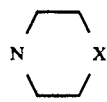

wherein X is defined above;

$R_{31}$ is hydrogen, loweralkyl, arylloweralkyl or hydroxyl;

$R_{33}$, $R_{34}$ and $R_{35}$ are the same or not all the same and each is hydrogen or loweralkyl;

Ar is phenyl, naphthyl, pyridinyl, pyridazinyl or pyrimidinyl, each of which is unsubstituted or mono- or poly-substituted by loweralkyl, halogen or nitro;

Ar' is phenyl, naphthyl, pyridinyl, pyridazinyl, pyrimidinyl, furanyl, oxazolyl, purinyl or thiazolyl, each of which is unsubstituted or mono- or poly-substituted by loweralkyl, halogen, nitro, or a group of formula $NR_{34'}R_{35'}$, or phenyl, naphthyl, pyridinyl or pyrimidinyl, each of which is mono- or poly-substituted by a group of formula $NR_{34'}R_{35'}$;

$R_{34'}$ and $R_{35'}$ are the same or different and each is hydrogen, loweralkyl or alkylaminoloweralkyl;

$R_{34'}$ and $R_{35'}$ taken together with the nitrogen atom to which they are attached form a group of formula

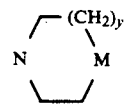

wherein M is $NR_{47}$, O or $CH_2$ and y is 0, 1 or 2;

Z is a group of formula $(CH_2)_vNR_{37}R_{38}$ wherein v is 0 or an integer from 2 to 5, a group of formula $N=CR_{39}R_{40}$ or a group of formula $(CH_2)_gCO_2H$ wherein g is an integer from 0 to 5;

Z and $R_{17}$ and the nitrogen to which they are attached form a group

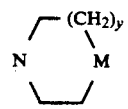

wherein M is $NR_{47}$, O or $CH_2$ and y is 0, 1 or 2;

$R_{37}$ and $R_{38}$ are the same or different and each is hydrogen, loweralkyl or a group of formula $COR_{41}$;

$R_{37}$ and $R_{38}$ taken together with a nitrogen atom to which they are attached form a group of formula

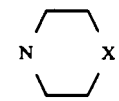

wherein X is defined as above;

$R_{39}$ is loweralkyl;

$R_{40}$ is loweralkyl, loweralkenyl, a group of formula

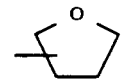

or a group of formula

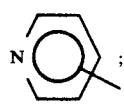

$R_{39}$ and $R_{40}$ taken together with the carbon atom to which they are attached form a group of formula

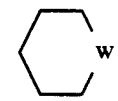

wherein W is O, a group of the formula $NR_{42}$, or a group of formula $CHR_{43}$;

$R_{41}$ s loweralkyl or a group of formula $(CH_2)_xNR_{44}R_{45}$ wherein x is an integer from 0 to 5;

$R_{42}$ is loweralkyl;

$R_{43}$ is hydrogen, loweralkyl or a group of formula $OR_{46}$;

$R_{44}$ and $R_{45}$ are the same or different and each is loweralkyl;

$R_{46}$ is loweralkyl;

$R_{47}$ is hydrogen, loweralkyl or (C=O) loweralkyl; and the optical and geometric isomers thereof, or a pharmaceutically acceptable salt thereof, provided:

(a) if $R_6$ is hydrogen, then $R_7$ is not hydrogen;
(b) if $R_7$ is hydrogen, hen $R_6$ is not hydrogen; and
(c) if neither $R_6$ nor $R_7$ is hydrogen, then $R_6$ is OH, $R_{13}(C(=O)O$, a group of formula $OR_{12}$, a group of formula $OCONR_{14}R_{15}$ or a group of formula OAr, and $R_7$ is

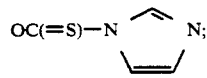

or, $R_6$ and $R_7$ taken together form a group of formula O—C(=S)—O.

5. A method for treating glaucoma in mammals comprising administering to a mammal requiring treatment for glaucoma a glaucoma treating effective amount of a composition comprising an inert adjuvant and a pharmaceutically effective amount of a compound of formula

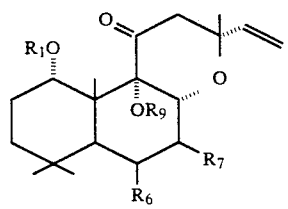

wherein $R_1$ is hydrogen, loweralkyl arylloweralkyl, a group of formula $R_2R_3R_4Si$, a group of formula $R_5CO$, a group of formula $R_8R_{10}N(CHR_{11})_nCO$ wherein n is 0 or 1, or Ar';

$R_6$ is hydrogen, hydroxyl, a group of formula $OR_{12}$, a group of formula $OCOR_{13}$, a group of formula $OCONR_{14}R_{15}$, or a group of formula OAr;

$R_7$ is defined as $R_6$, or is a group of formula $OCOR_{16}$, a group of formula $OCONR_{17}Z$, a group of formula OAr', a group of formula OCOAr', a group of formula $OCONR_{17}Ar'$, or a group of formula

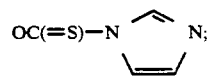

$R_6$ and $R_7$ taken together form a group of formula O—C(=S)—O;

$R_9$ is hydrogen;

or $R_1$ and $R_9$ may be taken together to form a group of formula CO, or a group of formula SO or a group of formula $CHNR_{18}R_{19}$;

$R_2$, $R_3$, and $R_4$ are the same or not all the same and each is loweralkyl;

$R_5$ is hydrogen or loweralkyl;

$R_8$, $R_{10}$ and $R_{11}$ are the same or not all the same and each is hydrogen, loweralkyl or arylloweralkyl;

$R_8$ and $R_{10}$ taken together with the nitrogen atom to which they are attached form a group of formula

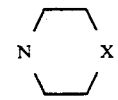

wherein

X is CO, O, S, a group of formula $CHR_{20}$ or a group of formula $NR_{21}$;

$R_{12}$ is loweralkyl or alkylaminoloweralkyl;

$R_{13}$ is hydrogen, straight or branched chain alkyl containing from 1 to 20 carbon atoms, —CH(OH)CH$_2$OH,

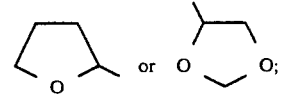

$R_{14}$ is hydrogen, loweralkyl, hydroxyloweralkyl, loweralkoxyloweralkyl, or a group of formula HOCH$_2$CH(OH)CH$_2$;

$R_{15}$ is hydrogen, hydroxyl, loweralkoxy, loweralkyl, hydroxyloweralkyl, loweralkoxyloweralkyl, loweralkanoyl, loweralkanoylloweralkyl, a group of formula

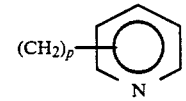

wherein p is 1 or 2, a group of formula

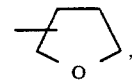

a group of formula HOCH$_2$(OH)CH$_2$, a group of formula $(CH_2)_qNR_{22}R_{23}$ wherein q is an integer equalling 0 or from 2 to 6, a group of formula $OR_{24}$ or a group of formula $OCOR_{25}$;

$R_{16}$ is hydroxyloweralkyl,

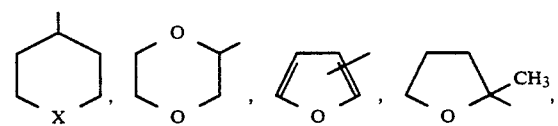

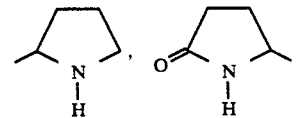

wherein X is as defined above, a group of formula $R_{26}OCR_{27}R_{28}(CH_2)_r$ wherein r is 0, 1, 2 or 3, a group of formula $R_{29}R_{30}N(CH_2)_s(CHR_{31})(CH_2)_{s'}$, wherein s and s' are the same or different and each is 0, 1 or 2, or a group of formula $(CH_2)_fCO_2H$, wherein f is an integer from 0 through 5;

$R_{17}$ is hydrogen or loweralkyl;

$R_{18}$ and $R_{19}$ are the same or different and each is loweralkyl;

$R_{18}$ and $R_{19}$ taken together with the nitrogen atom to which they are attached form a group of formula

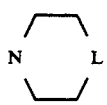

wherein L is O, S or $CHR_{20}$;
$R_{20}$ is hydrogen or loweralkyl;
$R_{21}$ is hydrogen or loweralkyl;
$R_{22}$ and $R_{23}$ are the same or different and each is loweralkyl;
$R_{22}$ and $R_{23}$ taken together with the nitrogen atom to which they are attached form a group of formula

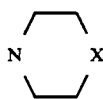

wherein X is defined as above;
$R_{24}$ is hydrogen, loweralkyl a group of formula $(CH_2)_q NR_{22}R_{23}$ wherein $R_{22}$, $R_{23}$ and q are as defined above;
$R_{25}$ is hydrogen, loweralkyl, lowercycloalkyl of 3 to 6 carbon atoms, haloloweralkenyl, loweralkanoylloweralkyl, loweralkoxyloweralkyl, loweralkoxycarbonylloweralkyl, loweralkylamino, lowerdialkylamino, a group of formula

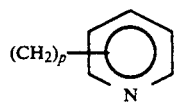

wherein p is defined as above, a group of formula

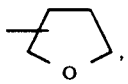

a group of the formula $(CH_2)_q NR_{22}R_{23}$ wherein $R_{22}$, $R_{23}$ and q are as defined above, a group of formula

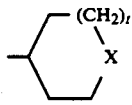

wherein x is as defined above and t is 0 or 1, or a group of formula $(CH_2)_u N(R_{33})COR_{34}$ wherein u is 1, 2 or 3;
$R_{26}$, $R_{27}$ and $R_{28}$ are the same or not all the same and each is hydrogen or loweralkyl;
$R_{29}$ is hydrogen, loweralkyl, or a group of formula $R_{35}CO$;
$R_{30}$ is hydrogen or loweralkyl;
$R_{29}$ and $R_{30}$ taken together with the nitrogen atom to which they are attached form a group of formula

wherein X is defined above;
$R_{31}$ is hydrogen, loweralkyl, arylloweralkyl or hydroxyl;
$R_{33}$, $R_{34}$ and $R_{35}$ are the same or not all the same and each is hydrogen or loweralkyl;
Ar is phenyl, naphthyl, pyridinyl, pyridazinyl or pyrimidinyl, each of which is unsubstituted or mono- or poly-substituted by loweralkyl, halogen or nitro;
Ar' is phenyl, naphthyl, pyridinyl, pyridazinyl, pyrimidinyl, furanyl, oxazolyl, purinyl or thiazolyl, each of which is unsubstituted or mono- or poly-substituted by loweralkyl, halogen, nitro, or a group of formula $NR_{34'}R_{35'}$, or phenyl, naphthyl, pyridinyl or pyrimidinyl, each of which is mono- or poly-substituted by a group of formula $NR_{34'}R_{35'}$;
$R_{34'}$ and $R_{35'}$ are the same or different and each is hydrogen, loweralkyl or alkylaminoloweralkyl;
$R_{34'}$ and $R_{35'}$ taken together with the nitrogen atom to which they are attached form a group of formula

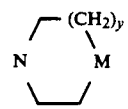

wherein M is $NR_{47}$, O or $CH_2$ and y is 0, 1 or 2;
Z is a group of formula $(CH_2)_v NR_{37}R_{38}$ wherein v is 0 or an integer from 2 to 5, a group of formula $N=CR_{39}R_{40}$ or a group of formula $(CH_2)_g CO_2 H$ wherein g is an integer from 0 to 5;
Z and $R_{17}$ and the nitrogen to which they are attached form a group

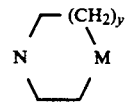

wherein M is $NR_{47}$, O or $CH_2$ and y is 0, 1 or 2;
$R_{37}$ and $R_{38}$ are the same or different and each is hydrogen, loweralkyl or a group of formula $COR_{41}$;
$R_{37}$ and $R_{38}$ taken together with a nitrogen atom to which they are attached form a group of formula

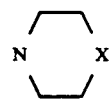

wherein X is defined as above;
$R_{39}$ is loweralkyl;
$R_{40}$ is loweralkyl, loweralkenyl, a group of formula

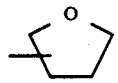

or a group of formula

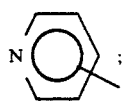

$R_{39}$ and $R_{40}$ taken together with the carbon atom to which they are attached form a group of formula

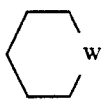

wherein W is O, a group of the formula $NR_{42}$, or a group of formula $CHR_{43}$;
$R_{41}$ s loweralkyl or a group of formula $(CH_2)_xNR_{44}R_{45}$ wherein x is an integer from 0 to 5;
$R_{42}$ is loweralkyl;
$R_{43}$ is hydrogen, loweralkyl or a group of formula $OR_{46}$;
$R_{44}$ and $R_{45}$ are the same or different and each is loweralkyl;
$R_{46}$ is loweralkyl;
$R_{47}$ is hydrogen, loweralkyl or (C=O) loweralkyl; and
the optical and geometric isomers thereof, or a pharmaceutically acceptable salt thereof, provided:
(a) if $R_6$ is hydrogen, then $R_7$ is not hydrogen;
(b) if $R_7$ is hydrogen, hen $R_6$ is not hydrogen; and
(c) if neither $R_6$ nor $R_7$ is hydrogen, then $R_6$ is OH, $R_{13}(C=O)O$, a group of formula $OR_{12}$, a group of formula $OCONR_{14}R_{15}$ or a group of formula OAr, and $R_7$ is

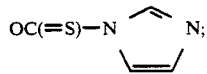

or, $R_6$ and $R_7$ taken together form a group of formula O—C(=S)—O.

6. A method for treating psoriasis in mammals comprising administering to a mammal requiring treatment for psoriasis a psoriasis treating effective amount of a composition comprising an inert adjuvant and a pharmaceutically effective amount of a compound of formula

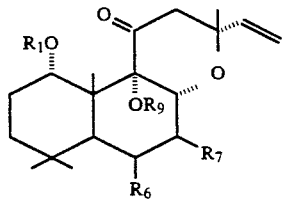

wherein
$R_1$ is hydrogen, loweralkyl arylloweralkyl, a group of formula $R_2R_3R_4Si$, a group of formula $R_5CO$, a group of formula $R_8R_{10}N(CHR_{11})_nCO$ wherein n is 0 or 1, or Ar';
$R_6$ is hydrogen, hydroxyl, a group of formula $OR_{12}$, a group of formula $OCOR_{13}$, a group of formula $OCONR_{14}R_{15}$, or a group of formula OAr;

$R_7$ is defined as $R_6$, or is a group of formula $OCOR_{16}$, a group of formula $OCONR_{17}Z$, a group of formula OAr', a group of formula OCOAr', a group of formula $OCONR_{17}Ar'$, or a group of formula

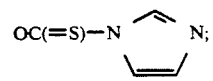

$R_6$ and $R_7$ taken together form a group of formula O—C(=S)—O;
$R_9$ is hydrogen;
or $R_1$ and $R_9$ may be taken together to form a group of formula CO, or a group of formula SO or a group of formula $CHNR_{18}R_{19}$;
$R_2$, $R_3$, and $R_4$ are the same or not all the same and each is loweralkyl;
$R_5$ is hydrogen or loweralkyl;
$R_8$, $R_{10}$ and $R_{11}$ are the same or not all the same and each is hydrogen, loweralkyl or arylloweralkyl;
$R_8$ and $R_{10}$ taken together with the nitrogen atom to which they are attached form a group of formula

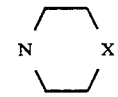

wherein
X is CO, O, S, a group of formula $CHR_{20}$ or a group of formula $NR_{21}$;
$R_{12}$ is loweralkyl or alkylaminoloweralkyl;
$R_{13}$ is hydrogen, straight or branched chain alkyl containing from 1 to 20 carbon atoms, —CH(OH)CH$_2$OH,

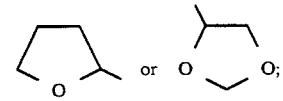

$R_{14}$ is hydrogen, loweralkyl, hydroxyloweralkyl, loweralkoxyloweralkyl, or a group of formula HOCH$_2$CH(OH)CH$_2$;
$R_{15}$ is hydrogen, hydroxyl, loweralkoxy, loweralkyl, hydroxyloweralkyl, loweralkoxyloweralkyl, loweralkanoyl, loweralkanoylloweralkyl, a group of formula

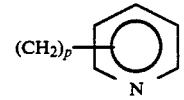

wherein p is 1 or 2, a group of formula

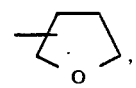

a group of formula HOCH$_2$(OH)CH$_2$, a group of formula $(CH_2)_qNR_{22}R_{23}$ wherein q is an integer equalling 0 or from 2 to 6, a group of formula $OR_{24}$ or a group of formula $OCOR_{25}$;
$R_{16}$ is hydroxyloweralkyl,

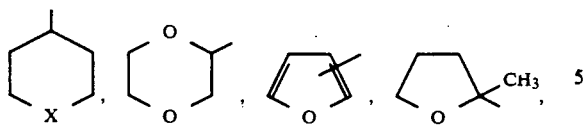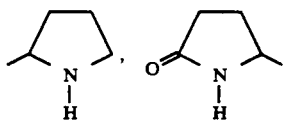

wherein X is as defined above, a group of formula $R_{26}OCR_{27}R_{28}(CH_2)_r$, wherein r is 0, 1, 2 or 3, a group of formula $R_{29}R_{30}N(CH_2)_s(CHR_{31})(CH_2)_{s'}$, wherein s and s' are the same or different and each is 0, 1 or 2, or a group of formula $(CH_2)_fCO_2H$, wherein f is an integer from 0 through 5;

$R_{17}$ is hydrogen or loweralkyl;

$R_{18}$ and $R_{19}$ are the same or different and each is loweralkyl;

$R_{18}$ and $R_{19}$ taken together with the nitrogen atom to which they are attached form a group of formula

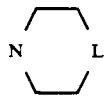

wherein L is O, S or $CHR_{20}$;

$R_{20}$ is hydrogen or loweralkyl;

$R_{21}$ is hydrogen or loweralkyl;

$R_{22}$ and $R_{23}$ are the same or different and each is loweralkyl;

$R_{22}$ and $R_{23}$ taken together with the nitrogen atom to which they are attached form a group of formula

wherein X is defined as above;

$R_{24}$ is hydrogen, loweralkyl a group of formula $(CH_2)_qNR_{22}R_{23}$ wherein $R_{22}$, $R_{23}$ and q are as defined above;

$R_{25}$ is hydrogen, loweralkyl, lowercycloalkyl of 3 to 6 carbon atoms, haloloweralkenyl, loweralkanoyl-loweralkyl, loweralkoxyloweralkyl, loweralkoxycarbonylloweralkyl, loweralkylamino, lowerdialkylamino, a group of formula

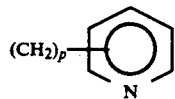

wherein p is defined as above, a group of formula

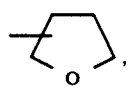

a group of the formula $(CH_2)_qNR_{22}R_{23}$ wherein $R_{22}$, $R_{23}$ and q are as defined above, a group of formula

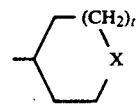

wherein x is as defined above and t is 0 or 1, or a group of formula $(CH_2)_uN(R_{33})COR_{34}$ wherein u is 1, 2 or 3;

$R_{26}$, $R_{27}$ and $R_{28}$ are the same or not all the same and each is hydrogen or loweralkyl;

$R_{29}$ is hydrogen, loweralkyl, or a group of formula $R_{35}CO$;

$R_{30}$ is hydrogen or loweralkyl;

$R_{29}$ and $R_{30}$ taken together with the nitrogen atom to which they are attached form a group of formula

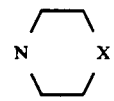

wherein X is defined above;

$R_{31}$ is hydrogen, loweralkyl, arylloweralkyl or hydroxyl;

$R_{33}$, $R_{34}$ and $R_{35}$ are the same or not all the same and each is hydrogen or loweralkyl;

Ar is phenyl, naphthyl, pyridinyl, pyridazinyl or pyrimidinyl, each of which is unsubstituted or mono- or poly-substituted by loweralkyl, halogen or nitro;

Ar' is phenyl, naphthyl, pyridinyl, pyridazinyl, pyrimidinyl, furanyl, oxazolyl, purinyl or thiazolyl, each of which is unsubstituted or mono- or poly-substituted by loweralkyl, halogen, nitro, or a group of formula $NR_{34'}R_{35'}$, or phenyl, naphthyl, pyridinyl or pyrimidinyl, each of which is mono- or poly-substituted by a group of formula $NR_{34'}R_{35'}$;

$R_{34'}$ and $R_{35'}$ are the same or different and each is hydrogen, loweralkyl or alkylaminoloweralkyl;

$R_{34'}$ and $R_{35'}$ taken together with the nitrogen atom to which they are attached form a group of formula

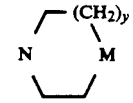

wherein M is $NR_{47}$, O or $CH_2$ and y is 0, 1 or 2;

Z is a group of formula $(CH_2)_vNR_{37}R_{38}$ wherein v is 0 or an integer from 2 to 5, a group of formula $N=CR_{39}R_{40}$ or a group of formula $(CH_2)_gCO_2H$ wherein g is an integer from 0 to 5;

Z and $R_{17}$ and the nitrogen to which they are attached form a group

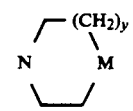

wherein M is $NR_{47}$, O or $CH_2$ and y is 0, 1 or 2;

$R_{37}$ and $R_{38}$ are the same or different and each is hydrogen, loweralkyl or a group of formula $COR_{41}$;

$R_{37}$ and $R_{38}$ taken together with a nitrogen atom to which they are attached form a group of formula

wherein X is defined as above;

$R_{39}$ is loweralkyl;

$R_{40}$ is loweralkyl, loweralkenyl, a group of formula

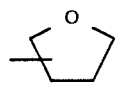

or a group of formula

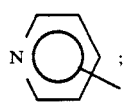

$R_{39}$ and $R_{40}$ taken together with the carbon atom to which they are attached form a group of formula

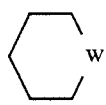

wherein W is O, a group of the formula $NR_{42}$, or a group of formula $CHR_{43}$;

$R_{41}$ s loweralkyl or a group of formula $(CH_2)_x NR_{44} R_{45}$ wherein x is an integer from 0 to 5;

$R_{42}$ is loweralkyl;

$R_{43}$ is hydrogen, loweralkyl or a group of formula $OR_{46}$;

$R_{44}$ and $R_{45}$ are the same or different and each is loweralkyl;

$R_{46}$ is loweralkyl;

$R_{47}$ is hydrogen, loweralkyl or (C=O) loweralkyl; and the optical and geometric isomers thereof, or a pharmaceutically acceptable salt thereof, provided:

(a) if $R_6$ is hydrogen, then $R_7$ is not hydrogen;
(b) if $R_7$ is hydrogen, hen $R_6$ is not hydrogen; and
(c) if neither $R_6$ nor $R_7$ is hydrogen, then $R_6$ is OH, $R_{13}(C(=O)O$, a group of formula $OR_{12}$, a group of formula $OCONR_{14}R_{15}$ or a group of formula OAr, and $R_7$ is

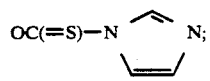

or, $R_6$ and $R_7$ taken together form a group of formula O—C(=S)—O.

7. A process for the preparation of a compound of formula

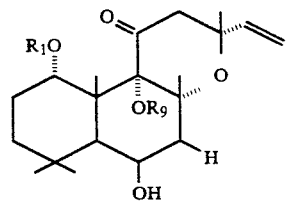

wherein $R_1$ and $R_9$ is hydrogen, the optical and geometric isomers thereof, or a pharmaceutically acceptable salt thereof, which comprises:

(a) contacting a compound of formula

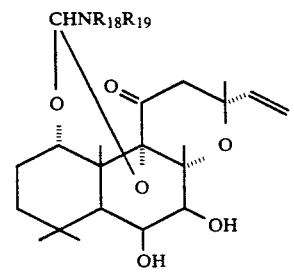

wherein $R_{18}$ and $R_{19}$ are the same or different and each is loweralkyl;

$R_{18}$ and $R_{19}$ taken together with the nitrogen atom to which they are attached form a group of formula

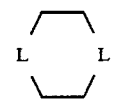

wherein L is O, S or a group of formula $CHR_{20}$;

$R_{20}$ is hydrogen or loweralkyl; with a compound of formula

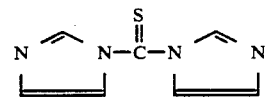

to provide a compound of formula

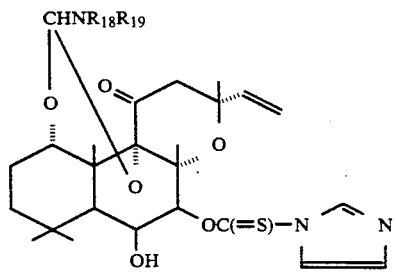

(b) contacting the product of step (a) with a trialkyltin hydride to provide a compound of formula

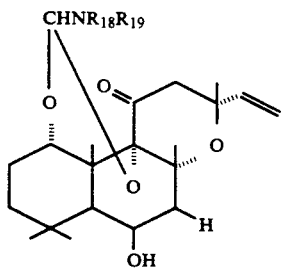

and (c) deacetalating the product of step (b).

8. The process of claim 7 wherein said trialkyltin hydride is tri-n-butyltin hydride.

9. The process of claim 7, wherein a catalyst is employed in step (a).

10. The process of claim 9 wherein said catalyst is 4-dimethylaminopyridine or 4-pyrrolidinopyridine.

11. The process of claim 7 wherein step (b) further comprises contacting the product of step (a) with a radical initiator and a trialkyltin hydride.

12. The process of claim 7 wherein the product of step (b) is deacetalated by treatment with a mixture of an alkanol and water, a mixture of an alkanol, water and an alkanoic acid or with a mixture of an alkanol, water and a mineral acid.

13. The process of claim 12 wherein the alkanol is methanol.

14. The process of claim 7 wherein contact in step (a) is conducted at a temperature between about 25° and 120° C.

15. The process of claim 14 wherein said temperature is between about 60° and 65° C.

16. The process of claim 7 wherein the contact in step (b) is conducted at a temperature between about 90° and 130° C.

17. The process of claim 16 wherein said temperature is between about 100° to 115° C.

18. A process for the preparation of a compound of formula

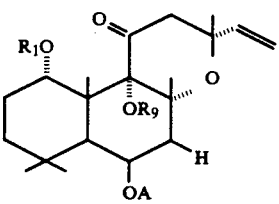

wherein $R_1$ and $R_9$ are hydrogen and A is acyl, the optical and geometric isomers thereof, or a pharmaceutically acceptable salt thereof which comprises:

(a) contacting a compound of formula

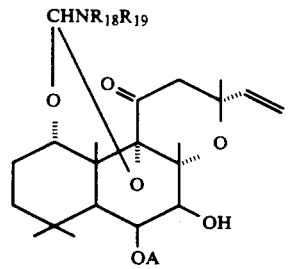

wherein $R_{18}$ and $R_{19}$ are the same or different and each is loweralkyl;

$R_{18}$ and $R_{19}$ taken together with the nitrogen atom to which they are attached form a group of formula

wherein L is O, S or a group of formula $CHR_{20}$;
$R_{20}$ is hydrogen or loweralkyl; with a compound of formula

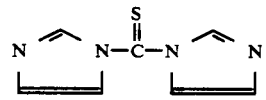

to provide a compound of formula

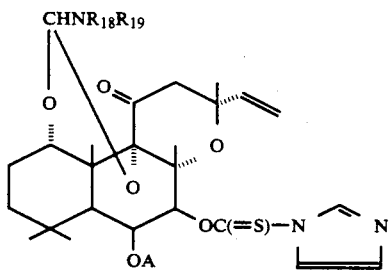

(b) contacting the product of step (a) with a trialkyltin hydride to provide a compound of formula

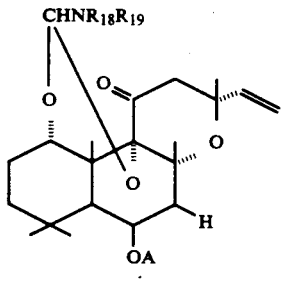

and (c) deacetalating the product of step (b).

19. The process of claim 18 wherein said trialkyltin hydride is tri-n-butyltin-hydride 20. The process of claim 18, wherein a catalyst is employed in step (a).

21. The process of claim 20, wherein said catalyst is 4-dimethylaminopyridine or 4-pyrrolidinopyridine.

22. The process of claim 18 wherein step (b) further comprises contacting the product of step (a) with a radical initiator and a trialkyltin hydride.

23. The process of claim 18 wherein the product of step (b) is deacetalated with by treatment with a mixture of an alkanol and water, a mixture of an alkanol, water and an alkanoic acid or a mixture of an alkanol, water and a mineral acid.

24. The process of claim 23 wherein the alkanol is methanol.

25. The process of claim 18 wherein contact in step (a) is conducted at a temperature between about 25° and 120° C.

26. The process of claim 25 wherein said temperature is between about 95° and 115° C.

27. The process of claim 18 wherein the contact in step (b) is conducted at a temperature between about 90° and 130° C.

28. The process of claim 27 wherein said temperature is between about 100° C.

* * * * *